United States Patent
Neumann et al.

(10) Patent No.: US 9,815,757 B2
(45) Date of Patent: Nov. 14, 2017

(54) PREPARATION OF ALDEHYDES AND KETONES FROM ALKENES USING POLYOXOMETALATE CATALYSTS AND NITROGEN OXIDES

(71) Applicant: YEDA RESEARCH AND DEVELOPMENT CO. LTD., Rehovot (IL)

(72) Inventors: Ronny Neumann, Kfar Saba (IL); Amir Rubinstein, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 0 days.

(21) Appl. No.: 15/123,252

(22) PCT Filed: Mar. 1, 2015

(86) PCT No.: PCT/IL2015/050221
§ 371 (c)(1),
(2) Date: Sep. 2, 2016

(87) PCT Pub. No.: WO2015/132780
PCT Pub. Date: Sep. 11, 2015

(65) Prior Publication Data
US 2017/0057897 A1   Mar. 2, 2017

Related U.S. Application Data

(60) Provisional application No. 61/946,806, filed on Mar. 2, 2014.

(51) Int. Cl.
| C07C 45/28 | (2006.01) |
| C07C 67/00 | (2006.01) |
| B01J 31/00 | (2006.01) |
| C07C 67/333 | (2006.01) |
| C07C 201/12 | (2006.01) |
| B01J 31/02 | (2006.01) |

(52) U.S. Cl.
CPC .......... *C07C 45/28* (2013.01); *B01J 31/0239* (2013.01); *B01J 31/0271* (2013.01); *C07C 67/333* (2013.01); *C07C 201/12* (2013.01); *B01J 2231/321* (2013.01); *B01J 2531/002* (2013.01)

(58) Field of Classification Search
CPC .... C07C 45/28; C07C 67/333; B01J 31/0239; B01J 31/0271
See application file for complete search history.

(56) References Cited

U.S. PATENT DOCUMENTS

| 6,060,419 A | * | 5/2000 | Wijesekera | ............ B01J 23/002 502/208 |
| 6,229,028 B1 | * | 5/2001 | Neumann | ............ B01J 23/6527 549/523 |

FOREIGN PATENT DOCUMENTS

| EP | 1078687 A1 | 2/2001 |
| WO | WO 98/54165 A1 | 12/1998 |
| WO | WO 00/43122 A1 | 7/2000 |
| WO | WO 03/028881 A1 | 4/2003 |
| WO | WO 2011/039744 A2 | 4/2011 |
| WO | WO 2012/059914 A1 | 5/2012 |
| WO | WO 2015/063763 A1 | 5/2015 |

OTHER PUBLICATIONS

Khenkin et al. Oxidation of Alkylarenes by Nitrate Catalyzed by Polyoxophospomolybdates: Synthetic Applications and Mechanistic Insights. Journal of the American Chemical Society, 2004, vol. 126, 6356-6362.*

Belanger et al. The interaction of nitrogen oxides with metal-oxygen cluster compounds (heteropoly oxometalates). Journal of Molecular Catalysis A: Chemical, 1996, vol. 114, 319-329.*

Addison et al. "533. Oxidation of dialkyl sulphides and trisubstituted phosphines by dinitrogen tetroxide; molecular addition compounds with dialkyl sulphoxides" Journal of the Chemical Society (Resumed). 1956:2705-8.

Afshar et al. "Stoichiometric and catalytic secondary O-atom transfer by Fe (III)-NO2 complexes derived from a planar tetradentate non-heme ligand: reminiscence of heme chemistry". Inorganic chemistry. Dec. 11, 2006;45(25):10347-54.

Andrews et al. "Synthesis, characterization, and equilibria of palladium (II) nitrile, alkene, and heterometallacyclopentane complexes involved in metal nitro catalyzed alkene oxidation reactions" Journal of the American Chemical Society, Oct. 1984;106(20):5913-20.

Andrews et al. "Transition-metal nitro-nitrosyl redox couple: catalytic oxidation of olefins to ketones" Journal of the American Chemical Society, May 1981;103(10):2894-6.

Bélanger et al. "The interaction of nitrogen oxides with metal-oxygen cluster compounds (heteropoly oxometalates)" Journal of Molecular Catalysis A: Chemical 114.1 (1996): 319-329.

Bosch et al. "Selective catalysis of thioether oxidations with dioxygen. Critical role of nitrosonium EDA Complexes in the thermal and photochemical transfer of oxygen atom from nitrogen oxides to sulfur centers" The Journal of Organic Chemistry. May 1995;60(10):3172-83.

Bosch et al. "Catalytic epoxidation of hindered olefins with dioxygen. Fast oxygen atom transfer to olefin cation radicals from nitrogen oxides" Journal of the American Chemical Society. Feb. 14, 1996;118(6):1319-29.

(Continued)

*Primary Examiner* — Sikarl Witherspoon
(74) *Attorney, Agent, or Firm* — Mark S. Cohen; Pearl Cohen Zedek Latzer Baratz LLP (57) ABSTRACT

The present invention relates to a process for preparing aldehydes and ketones by carbon-carbon bond cleavage of alkenes, wherein the process is catalysed by first row transition metal nitro coordinated polyoxometalate catalyst. The catalyst can be prepared by pre-treatment of aqua coordinated polyoxometalates with $NO_2$, or they are formed in situ when the reactions are carried in nitroalkanes under aerobic conditions, or they are formed in situ from nitrosyl (NO) compounds in the presence of $O_2$.

32 Claims, 4 Drawing Sheets

(56) References Cited

OTHER PUBLICATIONS

Bosch et al. "Electron-transfer catalysis of olefin epoxidation with nitrogen dioxide (dinitrogen tetroxide)" Journal of the Chemical Society, Chemical Communications. Jan. 1, 1993(8):667-8.
Castro et al. "Activation of nitrite ion by iron (III) porphyrins. Stoichiometric oxygen transfer to carbon, nitrogen, phosphorus, and sulfur" The Journal of Organic Chemistry. Apr. 1995;60(7):1922-3.
Davydov et al. "Generation of nitroxyl radicals in reactions of nitrogen dioxide with p-benzoquinones" Journal of the Chemical Society, Perkin Transactions 2. 2002(7):1359-63.
Ercolani, C.; Paoletti, A. M.; Pennesi, G.; Rossi, G. J. Chem. Soc. Dalton Trans. 1991, 1317-21.
Feltham RD "Transition metal complexes of NOx" Pure and Applied Chemistry. Jan. 1, 1989;61(5):943-6.
Field et al. "The preparation of aromatic aldehydes by means of the dinitrogen tetroxide reagent" Journal of the Chemical Society (Resumed). 1955:1110-2.
Heinecke et al. "Formation of cysteine sulfenic acid by oxygen atom transfer from nitrite" Journal of the American Chemical Society. Jun. 21, 2010;132(27);9240-3.
Horner et al. "Studien zum Ablauf der Substitution VI. Zum Verhalten tertiärer Amine und Thioäther gegen Stickstoffdioxyd" Justus Liebigs Annalen der Chemie. Mar. 10, 1953;579(3):193-203.
Khenkin et al. "Selective ortho hydroxylation of nitrobenzene with molecular oxygen catalyzed by the H5PV2Mo10O40 polyoxometalate" Journal of the American Chemical Society 127.28 (2005): 9988-9989.
Khenkin et al. "Oxidation of alkylarenes by nitrate catalyzed by polyoxophosphomolybdates: Synthetic applications and mechanistic insights" Journal of the American Chemical Society 126.20 (2004): 6356-6362.
Khin et al. "Oxygen atom transfer from nitrite mediated by Fe (III) porphyrins in aqueous solution" Journal of the American Chemical Society. Sep. 27, 2008;130(42):13830-1.
Kunieda et al. "The Reaction of Disulfide with Dinitrogen Tetroxide" Bulletin of the Chemical Society of Japan. 1968;41(1):233-.
Kurtikyan et al. "Six-Coordinate Nitro Complexes of Iron (III) Porphyrins with trans S-Donor Ligands. Oxo-Transfer Reactivity in the Solid State" Inorganic chemistry, Nov. 3, 2009;48(23):11236-41.
Lyon et al. "Highly oxidation resistant inorganic-porphyrin analog polyoxometalate oxidation catalysts. 1. The synthesis and characterization of aqueous-soluble potassium salts of. alpha. 2-P2W17O61 (Mn+. cntdot. OH2)(n-10) and organic solvent soluble tetra-n-butylammonium salts of. alpha. 2-P2W17O61 (Mn+. cntdot. Br )(n-11)(M= Mn3+, Fe3+, Co2+, Ni2+, Cu2+)" Journal of the American Chemical Society. Sep. 1991;113(19):7209-21.
Nyarady et al. "Selective catalytic oxidation of organic compounds by nitrogen dioxide" Journal of the American Chemical Society. Jun. 1985;107(12):3726-7.
Patra et al. "Thermally Induced Stoichiometric and Catalytic O-Atom Transfer by a Non-Heme Iron (III)—Nitro Complex: First Example of Reversible {Fe—NO} 7↔ FeIII-NO2 Transformation in the Presence of Dioxygen" Angewandte Chemie International Edition. Sep. 29, 2003;42(37):4517-21.
Rodriguez et al. "Oxidation kinetics of anthracene with nitrogen dioxide in acetic acid" The Canadian Journal of Chemical Engineering. Dec. 1, 1989;67(6):963-8.
Rubinstein et al. "Aerobic Carbon—Carbon Bond Cleavage of Alkenes to Aldehydes Catalyzed by First-Row Transition-Metal-Substituted Polyoxometalates in the Presence of Nitrogen Dioxide" Journal of the American Chemical Society 136.31 (2014): 10941-10948.
Seifert WK "Synthesis of Nitro-olefins from Olefin Dinitrogen Tetroxide Adducts1" The Journal of Organic Chemistry. Jan. 1963;28(1):125-9.
Shechter et al. "Orientation in Reactions of Dinitrogen Tetroxide and Methyl Acrylate1" Journal of the American Chemical Society. Nov. 1953;75(22):5610-3.
Shechter et al., "Stereochemistry of Addition of Dinitrogen Tetroxide to cis-and trans-Stilbenes" Journal of the American Chemical Society. Oct. 1959;81(20):5420-3.
Shechter et al. "Products and stereochemistry of reactions of dinitrogen tetroxide with. Delta. 9, 10-octalin, norbornene, cyclooctatetraene, 6, 6-diphenylfulvene, and indene" Journal of the American Chemical Society. Jun. 1967;89(12):3005-14.
Shiri et al. "Advances in the application of N 2 O 4/NO 2 in organic reactions" Tetrahedron. Nov. 20, 2010;66(47):9077-106.
Solar et al. "Selective Oxidations Using Metal Nitro-Complexes" Catalysis Reviews, Jan. 1, 1985;27(1):1-28.
Stepanov et al. "Reactions of alkenes with nitrogen oxides and other nitrosating and nitrating reagents" Russian chemical reviews. 2003;72(4):327-41.
Stevens TE. "Addition of Dinitrogen Tetroxide to Camphene and trans-Stibene; the Effect of Oxygen" Journal of the American Chemical Society. Jul. 1959;81(14):3593-7.
Suzuki et al. "Preference of the Mesolytic Cleavage over the Nuclear Substitution Observed in the Ozone-mediated Nitration of Bicumene with Nitrogen Dioxide. Implication to the Electron Transfer Nature of the Kyodai-Nitration of Arenes" Chemistry letters. 1996(8):647-8.
Taniguchi et al. "Multifunctionalization of alkenes via aerobic oxynitration and sp 3 C—H oxidation" Chemical Communications. 2013;49(22):2198-200.
Taniguchi et al. "Oxidative Nitration of Alkenes with Tert-Butyl Nitrite and Oxygen" Advanced Synthesis & Catalysis, Oct. 1, 2011;353(14-15):2643-7.
Tourné et al. "Chiral polytungstometalates [WM 3 (H 2 O) 2 (XW 9 O 34) 2] 12—(X= M= Zn or Co II) and their M-substituted derivatives. Syntheses, chemical, structural and spectroscopic study of some D, L sodium and potassium salts" Journal of the Chemical Society, Dalton Transactions. 1991(1):143-55.
Wickens et al. "Aldehyde-Selective Wacker-Type Oxidation of Unbiased Alkenes Enabled by a Nitrite Co-Catalyst" Angewandte Chemie. Oct. 18, 2013;125(43):11467-70.
International Search Report for PCT Application No. PCT/IL2015/050221 dated Aug. 18, 2015.

* cited by examiner

PREPARATION OF ALDEHYDES AND KETONES FROM ALKENES USING POLYOXOMETALATE CATALYSTS AND NITROGEN OXIDES

CROSS-REFERENCE TO RELATED APPLICATIONS

This application is a National Phase Application of PCT International Application No. PCT/IL2015/050221, International Filing Date Mar. 1, 2015, claiming priority and the benefit from U.S. Provisional Application Ser. No. 61/946,806, filed Mar. 2, 2014.

FIELD OF THE INVENTION

The present invention relates to a process for preparing aldehydes and ketones by carbon-carbon bond cleavage of alkenes, wherein the process is catalysed by first row transition metal nitro coordinated polyoxometalate catalyst.

BACKGROUND OF THE INVENTION

The aerobic cleavage of carbon-carbon double bonds of alkenes, especially to aldehydes, is a valuable transformation of synthetic importance. The use of renewable resources such as unsaturated fatty acid derivatives as feedstock substrates for such reactions is also enticing. High yields of carboxylic acids from disubstituted alkenes may be obtained using reagents such as permanganate/periodic acid, ruthenium tetraoxide with hypochlorite or periodate, and hydrogen peroxide with peroxotungstate catalysts under acidic conditions through formation of epoxide and diol intermediates. The strong oxidizing conditions used in these reactions typically prevent the selective preparation of aldehydes from disubstituted alkenes. For such transformations a common procedure is to utilize the 1,3-dipolar addition of ozone to a double bond to yield an initial ozonide or 1,2,3-trioxolane, which is then decomposed to yield aldehydes under reducing conditions. The explosive nature of ozone, often renders a multistep reaction cascade of epoxidation and hydrolysis to yield a glycol, which can then be cleaved by any number of procedures, as a more attractive alternative. Classically, periodic acid or lead acetate have often been used for the cleavage of glycols to aldehydes, but catalytic methods have also been disclosed including use of oxygen as oxidant.

It would be advantageous to use molecular oxygen, i.e., $O_2$, in a one-step oxidative cleavage of carbon-carbon bonds to yield aldehydes and/or ketones. However, the reaction of hydrocarbons with ground state $O_2$ ubiquitously occurs via free radical autooxidation mechanisms typically initiated by the cleavage of a carbon-hydrogen bond and formation of a carbon centered free radical, for example at the allylic position of an alkene. These mechanistically very complex autooxidation reactions, which involve the interplay of many reactions steps and multiple pathways, result in non-selective product formation, the bane of organic synthesis.

Paramagnetic nitrogen dioxide, $NO_2$, is a known reagent for nitration, nitrosation, and the facilitation of halogenation reactions; but also has been used for oxidation. The most reported oxidation reaction has been that of thioethers and other sulfur containing compounds. Typically, $NO_2$, a "weak" radical, is only active in hydrogen atom transfer reactions when the carbon-hydrogen bond is weak as in alcohols, although electron transfer oxidation of reactive substrates such as anthracene and polyhydroxyarenes is also known. As pertains to the reaction of $NO_2$ with alkenes, commonly addition to the double bond to yield nitroalkenes was observed. In certain cases, epoxidation has been observed such as with diadamantylidene and related hindered alkenes, and the reaction of phenylethenes with $NO_2$ has been reported to yield some carbon-carbon bond cleavage products, although the selectivity and yields are low.

To the Applicant's best knowledge, the selective cleavage of carbon-carbon double bonds with metal-nitro or metal-nitrito complexes has not been reported. In fact, metal-nitro and metal-nitrito compounds have been used only relatively rarely as oxygen donors. Thus, palladium-nitro catalysed oxidation of alkenes and iron heme and non-heme sulfoxidation of thioethers are the most reported transformations. Recently, nitrites have also been used as oxygen donors in the anti-Markovnikov palladium catalysed Wacker reaction.

There remains a need for efficient methods for preparing aldehydes and ketones by carbon-carbon bond cleavage of alkenes, which methods are amenable for industrial applications, as well as the use of renewable carbon sources as substrates.

SUMMARY OF THE INVENTION

The present invention relates to a process for preparing aldehydes and ketones by carbon-carbon bond cleavage of alkenes, wherein the process is catalysed by first row transition metal nitro coordinated polyoxometalates. The catalyst is formed in situ in the alkene reaction mixture or independent from the alkene reaction mixture. In one embodiment, the catalyst is formed by reacting a polyoxometalate precatalyst having an aqua or other ligand-coordinated polyoxometalates with $NO_2$ or its dimer $N_2O_4$, or the catalyst is formed by reacting under aerobic conditions polyoxometalate precatalyst and nitroalkane in the presence of molecular oxygen ($O_2$), or the catalyst is formed by reacting nitrosyl (NO) coordinated transition metal polyoxometalate precatalyst with oxygen ($O_2$) or under aerobic conditions.

The present invention is based on the unexpected discovery that nitro-ligated/coordinated polyoxometalate catalysts comprising at least one transition metal (TM), efficiently catalyse the cleavage of carbon-carbon double bonds, to produce high yield of carbonyl products. These reactions proceed via "TM-$NO_2$" species wherein $NO_2$ can be added initially as a gas or in the form of its dimer $N_2O_4$, or it can be formed from nitroalkanes in the presence of $O_2$. "TM-NO" species are formed after oxygen transfer and can be regenerated in the presence of $O_2$ to complete the catalytic cycle. Alternatively, "TM-NO" species can be prepared de novo and oxidized with an oxidant such as molecular oxygen ($O_2$) to yield a "TM-$NO_2$" species.

Thus, in one embodiment, the present invention relates to a process for the preparation of aldehydes and/or ketones from alkenes, comprising the step of contacting an alkene with a nitro coordinated polyoxometalate catalyst comprising a transition metal (TM), or a solvate thereof thereby generating the aldehydes and/or ketones. In some embodiments, the nitro coordinated polyoxometalate catalyst form a transition metal-$NO_2$ complex which catalyses C=C bond cleavage of the alkene, thereby generating the aldehydes and/or ketones.

In some embodiments, the nitro coordinated polyoxometalate is formed in situ in the alkene reaction mixture or independent from the alkene reaction mixture; wherein the nitro coordinated polyoxometalate is formed by reacting polyoxometalate precatalyst comprising transition metal (TM), or a solvate thereof with nitrogen dioxide (NO$_2$). The NO$_2$ is introduced into the reaction as a gas or in the form of its dimer N$_2$O$_4$. In accordance with this embodiment, the reaction may be conducted under aerobic or anaerobic conditions.

In other embodiments, the nitro coordinated polyoxometalate is formed in situ in the alkene reaction mixture or independent from the alkene reaction mixture; wherein the nitro coordinated polyoxometalate is formed by reacting under aerobic conditions polyoxometalate precatalyst and nitroalkane. In accordance with this embodiment, the alkene is reacted with an aqua (H$_2$O) or other ligand-coordinated polyoxometalate precatalyst in the presence of a nitroalkane and molecular oxygen (O$_2$), wherein the nitroalkane decomposes to generate NO$_2$ in situ. The nitroalkane is generally represented by the structure RNO$_2$ wherein R is a C$_1$-C$_3$ alkyl. Preferably, R is methyl (i.e., nitromethane) or ethyl (i.e., nitroethane).

In other embodiments, the nitro coordinated catalyst is formed in situ in the alkene reaction mixture or independent from the alkene reaction mixture; wherein the nitro coordinated polyoxometalate is formed by reacting nitrosyl (NO) coordinated polyoxometalate precatalyst with oxygen (O$_2$) or under aerobic conditions. Alternatively, the process of the invention results in a nitrosyl (NO) coordinated polyoxometalate which is regenerated under aerobic conditions to produce a nitro (NO$_2$) coordinated polyoxometalate.

In some embodiment, the alkene is a linear or branched alkene. In another embodiment, the alkene is non cyclic. In another embodiment, the alkenes are from synthetic or natural-bio-renewable origin may be used in the process of the invention. The alkene may be a 1-monosubstituted alkene, 1,1-disubstituted alkene, a 1,2-disubstituted alkene, a 1,1,2-trisubstituted alkene or a 1,1,2,2-tetrasubstituted alkene.

In some embodiments, the alkene is represented by formula R$^1$R$^2$C=CR$^3$R$^4$ wherein R$^1$-R$^4$ is each independently H, optionally substituted C$_1$-C$_{20}$ alkyl, optionally substituted aryl, optionally substituted cycloalkyl, optionally substituted heterocycloalkyl, optionally substituted heteroaryl wherein at least one of R$^1$-R$^4$ is other than H. In other embodiments, the alkene is selected from the group consisting of PhC(CH$_3$)=CH$_2$, Ph$_2$C=CH$_2$, (Z)-PhHC=CHPh, (E)-PhHC=CHPh, and Ph$_2$C=CPh$_2$.

In addition, the alkene is a monounsaturated or polyunsaturated alkene. In another embodiment, the alkene is a linear or branched optionally substituted monounsaturated or polyunsaturated alkene. In some embodiment, the alkene is a mono or poly-unsaturated fatty acid or a fatty acid derivative, which is preferably derived from a natural source. Non-limiting examples of alkenes include monounsaturated fatty acids, polyunsaturated fatty acids, monounsaturated fatty alcohols, polyunsaturated fatty alcohols, monounsaturated acids, polyunsaturated acids, monounsaturated alcohols, polyunsaturated alcohols, monounsaturated amides, polyunsaturated amides, monounsaturated esters, polyunsaturated esters, monounsaturated nitriles and polyunsaturated nitriles, including all isomers thereof.

Polyoxometalate catalysts suitable for use in the present invention are typically represented by the general formula I Q$_q$[X$_x$M$_m$TM$_n$L$_l$O$_y$F$_z$] or a solvate thereof, wherein X is a metal or non-metal heteroatom, proton or a combination thereof; M are addenda atoms selected from the group consisting of tungsten (W), molybdenum (Mo), niobium (Nb), and vanadium (V), and any combination thereof; TM are transition metals such as chromium (Cr), iron (Fe), manganese (Mn), cobalt (Co), nickel, (Ni), copper (Cu), zinc (Zn), ruthenium (Ru), palladium (Pd), platinum (Pt), iridium (Ir), rhodium (Rh) and any combination thereof; L are ligands to the transition metal such as aqua (H$_2$O), hydroxyl (OH), halides or pseudohalides (e.g., F, Cl, Br, I, CN, SCN, OCN), nitrosyl (NO), nitro (NO$_2$), null and any combination thereof; Q is a counter-cation selected from the group consisting of an alkali metal cation, an alkaline earth metal cation, a transition metal cation, an organic cation, a substituted or unsubstituted quaternary ammonium cation, an adduct of a quaternary ammonium cation with NO$_2$, a quaternary phosphonium cation, an adduct of a quaternary phosphonium cation with NO$_2$, and any combination thereof; O is oxygen; F is fluorine; x is an integer between 0 and 6; m is an integer between 4 and 200; n is an integer between 1 and 10; l is an integer between 1 and 10; y is an integer between 5 and 1000; q is an integer between 0 and 30; and z is an integer between 0 and 20. Non-limiting examples of such catalysts are provided hereinbelow. In a currently preferred embodiment, the polyoxometalate catalyst is Q$_q${α$_2$-TM(L)P$_2$W$_{17}$O$_{61}$} or Q$_q${[(TM(L)]$_2$WZn(ZnW$_9$O$_{34}$)$_2$}; Q$_q${[(TM(L)]$_2$WZn(ZnW$_9$O$_{34}$)$_2$} or Q$_q${[(TM(L)]$_2$WCo(Co(CoW$_9$O$_{34}$)$_2$}; Q$_q${XTM(L)M$_{11}$O$_{39}$}; or Q$_q${X'H$_2$TM(L)W$_{17}$F$_6$O$_{55}$}; wherein X, TM, L, Q, M and q are as defined above and X' is Na.

Polyoxometalate precatalysts suitable for use in the present invention are typically represented by the general formula I Q$_q$[X$_x$M$_m$TM$_n$L$_l$O$_y$F$_z$] or a solvate thereof, wherein X is a metal, non-metal heteroatom, a proton or combination thereof; M are addenda atoms selected from the group consisting of tungsten (W), molybdenum (Mo), niobium (Nb), and vanadium (V), and any combination thereof; TM are transition metals such as chromium (Cr), iron (Fe), manganese (Mn), cobalt (Co), nickel, (Ni), copper (Cu), zinc (Zn), ruthenium (Ru), palladium (Pd), platinum (Pt), iridium (Ir), rhodium (Rh) and any combination thereof; L are ligands to the transition metal such as aqua (H$_2$O), hydroxyl (OH), halides or pseudohalides (e.g., F, Cl, Br, I, CN, SCN, OCN), nitrosyl (NO), null and any combination thereof; Q is a counter-cation selected from the group consisting of an alkali metal cation, an alkaline earth metal cation, a transition metal cation, an organic cation, a substituted or unsubstituted quaternary ammonium cation, a quaternary phosphonium cation, and any combination thereof; O is oxygen; F is fluorine; x is an integer between 0 and 6; m is an integer between 4 and 200; n is an integer between 1 and 10; l is an integer between 1 and 10; y is an integer between 5 and 1000; q is an integer between 0 and 30; and z is an integer between 0 and 20. Non-limiting examples of such catalysts are provided hereinbelow. In a currently preferred embodiment, the polyoxometalate precatalyst is Q$_q${(α$_2$-TM(L)P$_2$W$_{17}$O$_{61}$} or Q$_q${[(TM(L)]$_2$WZn(ZnW$_9$O$_{34}$)$_2$}; Q$_q${[(TM(L)]$_2$WZn(ZnW$_9$O$_{34}$)$_2$} or Q$_q${[(TM(L)]$_2$WCo(CoW$_9$O$_{34}$)$_2$}; Q$_q${XTM(L)M$_{11}$O$_{39}$}; or Q$_q${X'H$_2$TM(L)W$_{17}$F$_6$O$_{55}$}; wherein X, TM, L, Q, M and q are as defined above; and X' is Na.

The process of the invention can be performed in the presence of a variety of organic solvents. Non-limiting examples of suitable solvents include aromatic hydrocarbons (e.g., toluene, xylene), nitriles (e.g., acetonitrile), carboxylic acids (e.g., acetic acid or propionic acid), ketones (e.g. acetone), alcohols (e.g., methanol, ethanol, propanol, isopropanol), halogenated hydrocarbons (e.g., methylene chloride, chloroform), nitroalkanes (e.g. nitromethane or nitroethane), ethers (e.g., tetrahydrofuran, dimethyl ether, diethyl ether), dimethyl sulfoxide, amides (e.g., dimethylformamide, dimethylacetamide, N-methylpyrrolidinone), carboxylic acids (e.g., propionic acid), esters (e.g., methyl acetate, ethyl acetate), etc.

In one embodiment, this invention is directed to a nitro coordinated polyoxometalate catalyst represented by the following structure of formula I:

$$Q_q[X_xM_mTM_nL_lO_yF_z]$$ or a solvate thereof, wherein

X is a metal or non-metal heteroatom, a proton or any combination thereof;
M is an addenda atom selected from the group consisting of tungsten (W), molybdenum (Mo), niobium (Nb), and vanadium (V), and any combination thereof;
TM is a transition metal selected from the group consisting of chromium (Cr), iron (Fe), manganese (Mn), cobalt (Co), nickel (Ni), copper (Cu), zinc (Zn), ruthenium (Ru), palladium (Pd), platinum (Pt), iridium (Ir), rhodium (Rh) and any combination thereof;
L is nitrogen dioxide ($NO_2$);
Q is a counter-cation selected from the group consisting of an alkali metal cation, an alkaline earth metal cation, a transition metal cation, an organic cation, a substituted or unsubstituted quaternary ammonium cation, an adduct of said quaternary ammonium cation with $NO_2$, a substituted or unsubstituted quaternary phosphonium cation, an adduct of said quaternary phosphonium cation with $NO_2$, and any combination thereof;
O is oxygen;
F is fluorine;
x is an integer between 0 and 6;
m is an integer between 4 and 200;
n is an integer between 1 and 10;
l is an integer between 0 and 10;
y is an integer between 5 and 1000;
q is an integer between 0 and 30; and
z is an integer between 0 and 20.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will be understood and appreciated more fully from the following detailed description taken in conjunction with the appended figure.

DETAILED DESCRIPTION OF THE PRESENT INVENTION

In one embodiment, this invention is directed to a nitro coordinated polyoxometalate catalyst comprising a transition metal, or solvate thereof, and uses thereof for the preparation of aldehydes and/or ketones from alkenes.

Figure 7:
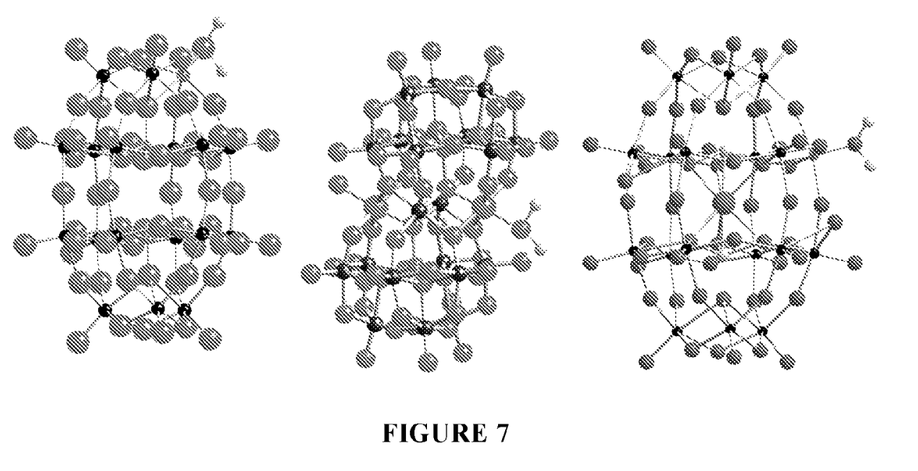
FIG. 7. Ball and stick structure representation for the WellsDawson $\{\alpha_2\text{-TM}(H_2O)P_2W_{17}O_{61}\}^{q-}$ (Left), the "Sandwich" $\{[(TM(H_2O)]_2WZn(ZnW_6O_{34})_2\}^{q-}$ (middle) and the Quasi Wells-Dawson $\{NaH_2TM(H_2O)W_{17}F_6O_{55}\}^{q-}$ Type Anions (right).

The present invention is based on part on the surprising discovery that reaction of $NO_2$ with a transition metal (TM)-substituted polyoxometalate yields a TM-nitro intermediate that was surprisingly competent for the oxidative cleavage of alkenes with formation of metal nitrosyl intermediates. The later could be re-oxidized with $O_2$ to yield a catalytic cycle as shown in Scheme 1. Scheme 1 shows aerobic oxidative cleavage of alkenes catalysed by transition metal polyoxometalates using, as an example, the Wells-Dawson $\{\alpha_2\text{-TM}(L)P_2W_{17}O_{61}\}^{8-}$, the "sandwich" type $\{[(TM(L)]_2WZn(ZnW_9O_{34})_2\}^{12-}$ or the Quasi Wells-Dawson $Q_q\{X'H_2TM(L)W_{17}F_6O_{55}\}$; (FIG. 7) catalytic systems, wherein TM is Cu, Zn, Fe, Mn, Co, Ni, and L is $NO_2$.

Scheme 1

In one embodiment, this invention is directed to a process for the preparation of aldehydes and/or ketones from alkenes, comprising the step of contacting said alkene with a nitro coordinated polyoxometalate catalyst comprising a transition metal (TM), or a solvate thereof, thereby generating the aldehydes and/or ketones. In another embodiment, the nitro coordinated polyoxometalate catalyst forms a transition metal-$NO_2$ complex which catalyses C=C bond cleavage of the alkene, thereby generating the aldehydes and/or ketones.

In one embodiment, this invention is directed to a process for the preparation of aldehydes and/or ketones from alkenes, comprising the step of contacting said alkene with polyoxometalate precatalyst comprising a transition metal (TM), or a solvate thereof, in the presence of nitrogen dioxide ($NO_2$), forming a nitro coordinated polyoxometalate catalyst, thereby generating the aldehydes and/or ketones. In another embodiment, the nitro coordinated polyoxometalate catalyst form a transition metal-NO$_2$ complex which catalyses C=C bond cleavage of the alkene, thereby generating the aldehydes and/or ketones.

In one embodiment, this invention is directed to a process for the preparation of aldehydes and/or ketones from alkenes, comprising the step of contacting said alkene with polyoxometalate precatalyst comprising a transition metal (TM), or a solvate thereof, in the presence of nitroalkane and oxygen, forming a nitro coordinated polyoxometalate catalyst, thereby generating the aldehydes and/or ketones.

In one embodiment, this invention is directed to a process for the preparation of aldehydes and/or ketones from alkenes, comprising the step of contacting said alkene with nitrosyl (NO) coordinated polyoxometalate precatalyst comprising a transition metal (TM), or a solvate thereof, in the presence of oxygen, forming a nitro coordinated polyoxometalate catalyst, thereby generating the aldehydes and/or ketones.

In some embodiments, the molar ratio of polyoxometalate to alkene is about 1 equivalent of polyoxometalate per alkene. In other embodiments, the molar ratio of polyoxometalate to alkene is about 0.1-1 equivalents of polyoxometalate per alkene. In other embodiments, the molar ratio of polyoxometalate to alkene is about 0.05 equivalent of polyoxometalate per alkene. In other embodiments, the molar ratio of polyoxometalate to alkene is about 0.02 equivalent of polyoxometalate per alkene. In other embodiments, the molar ratio of polyoxometalate to alkene is about 0.01 or less equivalent of polyoxometalate per alkene. Each possibility represents a separate embodiment of the present invention.

In some embodiments, the process of this invention is carried out under anaerobic conditions, while in one embodiment the reaction is carried out in the presence of oxygen ($O_2$). In some embodiment, the oxidation reaction is performed in the presence of molecular oxygen, hence in an atmosphere having at least partial pressure of $O_2$. In some embodiments, the oxidation reaction is performed in the presence of a predetermined and controllable partial pressure of $O_2$. According to some embodiments, partial pressure of $O_2$ in the atmosphere at which the reaction is performed ranges from 0.1 bar of $O_2$ to about 5 bar of $O_2$. In another embodiment, suitable oxygen pressures range from sub atmospheric $O_2$ pressure, to atmospheric pressure to about 2-3 bars $O_2$. It is noted herein that the reaction is not limited by its efficiency to 5 bar of $O_2$, and higher pressures are also suitable.

Polyoxometalate Catalysts/Precatalysts

In one embodiment, this invention is directed to a nitro coordinated polyoxometalate catalyst comprising a transition metal, or solvate thereof and uses thereof for the preparation of aldehydes and/or ketones from alkenes. The nitro coordinated polyoxometalate catalyst is a soluble polyoxoanion salt represented by the general formula $Q_q[X_xM_m TM_nL_lO_yF_z]$ or a solvate thereof, wherein X is a metal or non-metal heteroatom, a proton or combination thereof; M is an addenda atom selected from the group consisting of tungsten (W), molybdenum (Mo), niobium (Nb), and vanadium (V), and any combination thereof; TM is a transition metal selected from the group consisting of chromium (Cr), iron (Fe), manganese (Mn), cobalt (Co), nickel, (Ni), copper (Cu), zinc (Zn), ruthenium (Ru), palladium (Pd), platinum (Pt), iridium (Ir), rhodium (Rh) and any combination thereof; L is nitro ($NO_2$); Q is a counter-cation selected from the group consisting of an alkali metal cation, an alkaline earth metal cation, a transition metal cation, an organic cation, a substituted or unsubstituted quaternary ammonium cation, an adduct of said quaternary ammonium cation with $NO_2$, a substituted or unsubstituted quaternary phosphonium cation, an adduct of said quaternary phosphonium cation with $NO_2$, and any combination thereof; O is oxygen; F is fluorine; x is an integer between 0 and 6; m is an integer between 4 and 200; n is an integer between 1 and 10; l is an integer between 0 and 10; y is an integer between 5 and 1000; q is an integer between 0 and 30; and z is an integer between 0 and 20.

In some embodiments, the polyoxometalate catalyst is a Wells-Dawson type polyoxometalate represented by the structure $Q_q\{\alpha_2\text{-TM(L)}P_2W_{17}O_{61}\}$ or $Q_q\{\alpha_1\text{-TM(L)}P_2W_{17}O_{61}\}$ wherein Q, q, TM and L are as defined above. In some preferred embodiments of the Wells-Dawson type polyoxometalate:

TM is a transition metal selected from Cr, Mn, Fe, Co, Ni, Cu, Zn and Ru, preferably Ru, Fe, Mn, Co, Ni and Cu;

L is $NO_2$;

Q is a counter-cation selected from the group consisting of an alkali metal cation, an alkaline earth metal cation, a transition metal cation, an organic cation, a substituted or unsubstituted quaternary ammonium cation, an adduct of said quaternary ammonium cation with $NO_2$, a substituted or unsubstituted quaternary phosphonium cation, an adduct of said quaternary phosphonium cation with $NO_2$, and any combination thereof; and q is an integer between 6 and 12.

Examples of Wells-Dawson type polyoxometalate include, but are not limited to: $Q_8\{\alpha_2\text{-Cu}(NO_2)P_2W_{17}O_{61}\}$, $Q_8\{\alpha_1\text{-Cu}(NO_2)P_2W_{17}O_{61}\}$. Each possibility represents a separate embodiment of the present invention.

In other preferred embodiments, the polyoxometalate catalyst is a "sandwich" type polyoxometalate represented by the structure $Q_q\{[(\text{TM(L)})]_2WZn(ZnW_9O_{34})_2\}$ or $Q_q\{[(\text{TM(L)})]_2WCo(CoW_9O_{34})_2\}$ wherein Q, q, TM and L are as defined above. In some preferred embodiments of the "sandwich" type polyoxometalate:

TM is a transition metal selected from Cr, Mn, Fe, Co, Ni, Cu, Zn and Ru, preferably Ru, Fe, Mn, Co, Ni and Cu;

L is $NO_2$;

Q is a counter-cation selected from the group consisting of an alkali metal cation, an alkaline earth metal cation, a transition metal cation, an organic cation, a substituted or unsubstituted quaternary ammonium cation, an adduct of said quaternary ammonium cation with $NO_2$, a substituted or unsubstituted quaternary phosphonium cation, an adduct of said quaternary phosphonium cation with $NO_2$, and any combination thereof; and q is an integer between 6 and 12.

Examples of "sandwich" type polyoxometalate include, but are not limited to: $Q_{12}\{\text{ZnWCu}_2(NO_2)_2(ZnW_9O_{34})_2\}$, or $Q_{12}\{\text{CoWCu}_2(NO_2)_2(CoW_9O_{34})_2\}$. Each possibility represents a separate embodiment of the present invention.

In some embodiments, the polyoxometalate catalyst is a "Keggin" type polyoxometalate represented by the structure $Q_q\{XTM(L)M_{11}O_{39}\}$ wherein Q, q, X, TM, L and M are as defined above. In some preferred embodiments of the "Keggin" type polyoxometalate, X is P, Si or As; M is Mo, W or a combination thereof, and q is 3-10.

In some embodiments, the polyoxometalate catalyst is quasi Wells-Dawson polyfluoroxometalate type polyoxometalate represented by the structure $Q_q\{X'H_2TM(L)W_{17}F_6O_{55}\}$. In another embodiment, X' is Na, TM is Cu or Mn, and q is between 3 to 10. In another embodiment, $Q_q[X_xM_mTM_nL_lO_yF_z]$ is represented by the structure $Q_q\{X'H_2TM(L)W_{17}F_6O_{55}\}$; wherein X is X' and a proton and X' is Na; and M is W.

Examples of quasi Wells-Dawson polyfluoroxometalate type polyoxometalate catalyst include $Q_9\{NaH_2Cu(NO_2)W_{17}F_6O_{55}\}$ and $Q_9\{NaH_2Mn(NO_2)W_{17}F_6O_{55}\}$.

In another embodiment, Q substituents for any of the foregoing polyoxometalate catalysts are trioctylmethylammonium or $NO_2$ adducts thereof. Each possibility represents a separate embodiment of the present invention.

In another embodiment X substituents for any of the foregoing catalysts are Na, B, Al, Ga, In, Si, Ge, Sn, P, As, Sb, S, Se Te, a proton or any combination thereof. Each possibility represents a separate embodiment of the present invention.

In another embodiment X' substituents for any of the foregoing catalysts is Na.

In some embodiment, the process of this invention makes use of a precatalyst. In one embodiment, the precatalyst is used in situ, in the alkene reaction mixture. In one embodiment, the nitro coordinated polyoxometalate and its use in the process of the preparation of ketone and/or aldehyde is formed independent/separately from the alkene reaction mixture. In another embodiment, the nitro coordinated polyoxometalate is formed by reacting a precatalyst in the presence of $NO_2$ or $N_2O_4$. In another embodiment, the nitro coordinated polyoxometalate is formed by reacting under aerobic conditions polyoxometalate precatalyst and a nitroalkane. In another embodiment, the nitro coordinated polyoxometalate is formed by reacting a nitrosyl (NO) coordinated polyoxometalate precatalyst under aerobic conditions.

In one embodiment, the process of this invention makes use of a polyoxometalate precatalyst. In another embodiment, the precatalysts are soluble polyoxoanion salts represented by the general formula $Q_q[X_xM_mTM_nL_lO_yF_z]$ or a solvate thereof, wherein X is a metal, non-metal heteroatom, a proton or any combination thereof; M is an addenda atom selected from the group consisting of tungsten (W), molybdenum (Mo), niobium (Nb), and vanadium (V), and any combination thereof; TM is a transition metal selected from the group consisting of chromium (Cr), iron (Fe), manganese (Mn), cobalt (Co), nickel (Ni), copper (Cu), zinc (Zn), ruthenium (Ru), palladium (Pd), platinum (Pt), iridium (Ir), rhodium (Rh) and any combination thereof; L is absent or is a ligand selected from the group consisting of ($H_2O$), hydroxyl (OH), a halide selected from F, Cl, Br and I; a pseudohalide selected from CN, OCN and SCN; nitrosyl (NO) and any combination thereof; Q is a counter-cation selected from the group consisting of an alkali metal cation, an alkaline earth metal cation, a transition metal cation, an organic cation, a substituted or unsubstituted quaternary ammonium cation, a substituted or unsubstituted quaternary phosphonium cation, and any combination thereof; O is oxygen; F is fluorine; x is an integer between 0 and 6; m is an integer between 4 and 200; n is an integer between 1 and 10; l is an integer between 0 and 10; y is an integer between 5 and 1000; q is an integer between 0 and 30; and z is an integer between 0 and 20.

In some embodiments, the polyoxometalate precatalyst is a Wells-Dawson type polyoxometalate represented by the structure $Q_q\{\alpha_2\text{-TM(L)}P_2W_{17}O_{61}\}$ or $Q_q\{\alpha_1\text{-TM(L)}P_2W_{17}O_{61}\}$ wherein Q, q, TM and L are as defined above. In some preferred embodiments of the Wells-Dawson type polyoxometalate:

TM is a transition metal selected from Cr, Mn, Fe, Co, Ni, Cu, Zn and Ru, preferably Ru, Fe, Mn, Co, Ni and Cu;
L is $H_2O$ or NO;
Q is a counter-cation selected from the group consisting of an alkali metal cation, an alkaline earth metal cation, a transition metal cation, an organic cation, a substituted or unsubstituted quaternary ammonium cation, an adduct of said quaternary ammonium cation with $NO_2$, a substituted or unsubstituted quaternary phosphonium cation, an adduct of said quaternary phosphonium cation with $NO_2$, and any combination thereof; and
q is an integer between 6 and 12.

Examples of Wells-Dawson type polyoxometalate precatalyst include, but are not limited to: $Q_8\{\alpha_2\text{-Cu}(H_2O)P_2W_{17}O_{61}\}$, $Q_8\{\alpha_2\text{-Cu(NO)}P_2W_{17}O_{61}\}$, $Q_8\{\alpha_1\text{-Cu}(H_2O)P_2W_{17}O_{61}\}$ and $Q_8\{\alpha_1\text{-Cu(NO)}P_2W_{17}O_{61}\}$. Each possibility represents a separate embodiment of the present invention.

In other preferred embodiments, the polyoxometalate precatalyst is a "sandwich" type polyoxometalate represented by the structure $Q_q\{[(TM(L)]_2WZn(ZnW_9O_{34})_2\}$ or $Q_q\{[(TM(L)]_2WCo(CoW_9O_{34})_2\}$ wherein Q, q, TM and L are as defined above. In some preferred embodiments of the "sandwich" type polyoxometalate:

TM is a transition metal selected from Cr, Mn, Fe, Co, Ni, Cu, Zn and Ru, preferably Ru, Fe, Mn, Co, Ni and Cu;
L is $H_2O$ or NO;
Q is a counter-cation selected from the group consisting of an alkali metal cation, an alkaline earth metal cation, a transition metal cation, an organic cation, a substituted or unsubstituted quaternary ammonium cation, an adduct of said quaternary ammonium cation with $NO_2$, a substituted or unsubstituted quaternary phosphonium cation, an adduct of said quaternary phosphonium cation with $NO_2$, and any combination thereof; and
q is an integer between 6 and 12.

Examples of "sandwich" type polyoxometalate precatalyst include, but are not limited to: $Q_{12}\{ZnWCu_2(H_2O)_2(ZnW_9O_{34})_2\}$, $Q_{12}\{ZnWCu_2(NO)_2(ZnW_9O_{34})_2\}$, $Q_{12}\{CoWCu_2(H_2O)_2(CoW_9O_{34})_2\}$ or $Q_q\{CoWCu_2(NO)_2(CoW_9O_{34})_2\}$. Each possibility represents a separate embodiment of the present invention.

In other preferred embodiments, the polyoxometalate precatalyst is a "Keggin" type polyoxometalate represented by the structure $Q_q\{XTM(L)M_{11}O_{39}\}$ wherein Q, q, X, TM, L and M are as defined above. In some preferred embodiments of the "Keggin" type polyoxometalate, X is P, Si or As; M is Mo, W or a combination thereof, and q is 3-10.

In some embodiments, the polyoxometalate precatalyst is quasi Wells-Dawson polyfluoroxometalate type polyoxometalate represented by the structure $Q_q\{X'H_2TM(L)W_{17}F_6O_{55}\}$. In another embodiment, X' Na, TM is Cu or Mn, and q is between 3 to 10. In another embodiment, $Q_q[X_xM_mTM_nL_lO_y F_z]$ is represented by the structure $Q_q\{X'H_2TM(L)W_{17}F_6O_{55}\}$; wherein X is X' and a proton and X' is Na; and M is W.

Examples of quasi Wells-Dawson polyfluoroxometalate type polyoxometalate precatalyst include $Q_9\{NaH_2Cu(H_2O)W_{17}F_6O_{55}\}$, $Q_9\{NaH_2Mn(H_2O)W_{17}F_6O_{55}\}$, $Q_9\{NaH_2Cu(NO)W_{17}F_6O_{55}\}$ and $Q_9\{NaH_2Mn(NO)W_{17}F_6O_{55}\}$.

In another embodiment X' is Na.

Preferred X substituents for any of the foregoing precatalysts are Na, B, Al, Ga, In, Si, Ge, Sn, P, As, Sb, S, Se Te, a proton or any combination thereof. Each possibility represents a separate embodiment of the present invention.

The term "solvate" refers to a complex of variable stoichiometry (e.g., di-, tri-, tetra-, penta-, hexa-, and so on up to 1000-), which is formed by a solute (transition metal-polyoxometalate) and a solvent, whereby the solvent does not interfere with the activity of the solute. Suitable solvents and solvent mixture may include, for example, water, acetonitrile, ethanol, acetic acid and the like.

Polyoxometalate catalyst or precatalyst of this invention are often found in solvated forms, for example hydrates. Thus, the present invention encompasses polyoxometalate solvates, such as but not limited to polyoxometalate hydrates. Other solvate molecules of polyoxometalate include, but are not limited to diethylether, acetonitrile, dimethylsulfoxide, tetrahydrofuran, methanol, ethanol solvates and so forth. The amount of solvate molecules can vary from less than one to a few hundred. Each possibility represents a separate embodiment of the present invention.

The term "hydrate" refers to a solvate, as defined hereinabove, where the solvent is water. The number of water molecules in a hydrate can range from 1 and up to 1,000.

The polyoxometalate catalyst or precatalyst of this invention are represented by formula I: $Q_q[X_xM_mTML_lO_yF_z]$. In one embodiment, M is an addenda atom selected from the group consisting of tungsten (W), molybdenum (Mo), niobium (Nb), and vanadium (V), and any combination thereof In another embodiment, M is tungsten (W). In another embodiment, M molybdenum (Mo). In another embodiment, M niobium (Nb). In another embodiment, M and vanadium (V). In one embodiment, x is an integer between 0 and 6. In another embodiment, x is 0. In another embodiment, x is 1, in another embodiment, x is 2. In another embodiment x is 3. In another embodiment, x is 4. In another embodiment, x is 5. In another embodiment, x is 6. In one embodiment, m is an integer between 4 and 200. In another embodiment, m is 4. In another embodiment, m is between 5 to 10. In another embodiment, m is between 10 to 20. In another embodiment, m is between 20 to 40. In another embodiment, m is between 5 to 50. In another embodiment, m is between 20 to 100. In another embodiment, m is between 100 to 200. In another embodiment, m is between 50 to 150. In another embodiment, m is between 4 to 50. In another embodiment, m is between 4 to 100. In one embodiment, n is an integer between 1 and 10. In another embodiment, n is 1. In another embodiment, n is 2. In another embodiment, n is 3. In another embodiment, n is 4. In another embodiment, n is 5. In another embodiment, n is 6. In another embodiment, n is 7. In another embodiment, n is 8. In another embodiment, n is 9. In another embodiment, n is 10. In one embodiment, l is an integer between 0 and 10. In another embodiment, l is 0. In another embodiment, l is 1. In another embodiment, l is 2. In another embodiment, l is 3. In another embodiment, l is 4. In another embodiment, l is 5. In another embodiment, l is 6. In another embodiment, l is 7. In another embodiment, l is 8. In another embodiment, l is 9. In another embodiment, l is 10. In one embodiment, y is an integer between 5 and 1000. In another embodiment, y is an integer between 5 and 20. In another embodiment, y is an integer between 5 and 100. In another embodiment, y is an integer between 50 and 200. In another embodiment, y is an integer between 50 and 500. In another embodiment, y is an integer between 100 and 1000. In one embodiment q is an integer between 0 and 30. In another embodiment, q is 0. In another embodiment, q is an integer between 1 and 30. In another embodiment, q is an integer between 0 to 10. In another embodiment, q is an integer between 5 and 15. In one embodiment, z is an integer between 0 and 20. In another embodiment, z is 0. In another embodiment, z is an integer between 1-20. In another embodiment, z is an integer between 1 and 10. In another embodiment, z is an integer between 5 and 20. In another embodiment, z is an integer between 5 and 15.

The polyoxometalate catalyst or precatalyst of this invention include transition metals. In one embodiment, the transition metals (TM) may be in any oxidation state such as (II), (III), (IV) etc. In another embodiment, the transition metal is chromium (Cr). In another embodiment, the transition metal is iron (Fe). In another embodiment, the transition metal is manganese (Mn). In another embodiment, the transition metal is cobalt (Co). In another embodiment, the transition metal is nickel, (Ni). In another embodiment, the transition metal is copper (Cu). In another embodiment, the transition metal is zinc (Zn). In another embodiment, the transition metal is ruthenium (Ru). In another embodiment, the transition metal is palladium (Pd). In another embodiment, the transition metal is platinum (Pt). In another embodiment, the transition metal is iridium (Ir). In another embodiment, the transition metal is rhodium (Rh). In another embodiment, the transition metal is chromium (Cr), iron (Fe), manganese (Mn), cobalt (Co), nickel, (Ni), copper (Cu), zinc (Zn), ruthenium (Ru), palladium (Pd), platinum (Pt), iridium (Ir), rhodium (Rh) and any combination thereof or any combination thereof.

Alkenes

As mentioned above, the nature of the alkene substrate is not particularly limiting, and alkenes from synthetic or natural-bio-renewable origin may be used in the process of the invention. In one embodiment, the alkene is linear or branched alkene. In another embodiment, the alkene is non-cyclic. In another embodiment, the alkene is a linear or branched substituted monounsaturated or polyunsaturated alkene.

In another embodiment, the alkene is a 1-monosubstituted alkene, 1,1-disubstituted alkene, a 1,2-disubstituted alkene, a 1,1,2-trisubstituted alkene or a 1,1,2,2-tetrasub stituted alkene, wherein the substituents of the alkene include optionally substituted $C_1$-$C_{20}$ alkyl, optionally substituted aryl, optionally substituted cycloalkyl, optionally substituted heterocycloalkyl, optionally substituted heteroaryl. In another embodiment the substituents of the aryl, alkyl, cycloalkyl and heterocycle include one or more substituents including $NO_2$, CN, alkoxy, haloalkyl, halide, hydroxyl, thiol, amine, carboxylic acid, amide, ester or any combination thereof.

In some embodiments, the alkene is represented by formula $R^1R^2C=CR^3R^4$ wherein $R^1$-$R^4$ is each independently a H, optionally substituted $C_1$-$C_{20}$ alkyl, optionally substituted aryl, optionally substituted cycloalkyl, or optionally substituted heterocycle or any combination thereof, wherein at least one of $R^1$-$R^4$ is other than H. In another embodiment, the substituents of the aryl, alkyl, cycloalkyl and heterocycle include $NO_2$, CN, alkoxy, haloalkyl, halide, hydroxyl, thiol, amine, carboxylic acid, amide, ester or any combination thereof.

As used herein, the term "alkyl" can be any straight- or branched-chain alkyl group containing up to about 30 carbons unless otherwise specified. In another embodiment, an alkyl includes $C_1$-$C_5$ carbons. In another embodiment, an alkyl includes $C_1$-$C_6$ carbons. In another embodiment, an alkyl includes $C_1$-$C_8$ carbons. In another embodiment, an alkyl includes $C_1$-$C_{10}$ carbons. In another embodiment, an alkyl is a $C_1$-$C_{12}$ carbons. In another embodiment, an alkyl is a $C_1$-$C_{20}$ carbons. In another embodiment, branched alkyl is an alkyl substituted by alkyl side chains of 1 to 5 carbons. In one embodiment, the alkyl group may be unsubstituted. In another embodiment, the alkyl group may be substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl.

As used herein, the term "aryl" refers to any aromatic ring that is directly bonded to another group and can be either substituted or unsubstituted. The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkoxy, $C_1$-$C_5$ linear or branched haloalkoxy, $CF_3$, CN, $NO_2$, —$CH_2CN$, $NH_2$, NH-alkyl, N(alkyl)$_2$, hydroxyl.

As used herein, the term "alkoxy" refers to an ether group substituted by an alkyl group as defined above. Alkoxy refers both to linear and to branched alkoxy groups. Non-limiting examples of alkoxy groups are methoxy, ethoxy, propoxy, iso-propoxy, tert-butoxy.

A "haloalkyl" group refers, in another embodiment, to an alkyl group as defined above, which is substituted by one or more halogen atoms, e.g. by F, Cl, Br or I. Nonlimiting examples of haloalkyl groups are $CF_3$, $CF_2CF_3$, $CH_2CF_3$.

A "cycloalkyl" group refers, in one embodiment, to a ring structure comprising carbon atoms as ring atoms, which may be either saturated or unsaturated, substituted or unsubstituted. In another embodiment the cycloalkyl is a 3-12 membered ring. In another embodiment the cycloalkyl is a 6 membered ring. In another embodiment the cycloalkyl is a 5-7 membered ring. In another embodiment the cycloalkyl is a 3-8 membered ring. In another embodiment, the cycloalkyl group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the cycloalkyl ring may be fused to another saturated or unsaturated cycloalkyl or heterocyclic 3-8 membered ring. In another embodiment, the cycloalkyl ring is a saturated ring. In another embodiment, the cycloalkyl ring is an unsaturated ring. Non limiting examples of a cycloalkyl group comprise cyclohexyl, cyclohexenyl, cyclopropyl, cyclopropenyl, cyclopentyl, cyclopentenyl, cyclobutyl, cyclobutenyl, cyclooctyl, cyclooctadienyl (COD), cyclooctaene (COE) etc.

A "heterocycle" or "heterocyclic" group refers, in one embodiment, to a ring structure comprising in addition to carbon atoms, sulfur, oxygen, nitrogen or any combination thereof, as part of the ring. In another embodiment the heterocycle is a 3-12 membered ring. In another embodiment the heterocycle is a 6 membered ring. In another embodiment the heterocycle is a 5-7 membered ring. In another embodiment the heterocycle is a 3-8 membered ring. In another embodiment, the heterocycle group may be unsubstituted or substituted by a halogen, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycle ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. Non limiting examples of a heterocyclic rings comprise pyridine, piperidine, morpholine, piperazine, thiophene, pyrrole, benzodioxole, or indole.

The alkene substrates used in the process of the invention contain one or more double bonds. The present invention intends to encompass all structural and geometrical isomers including cis, trans, E and Z isomers, independently at each occurrence. Thus, the alkene may be a cis-alkene, trans-alkene, (Z) or (E) isomers, or combinations thereof.

In some embodiments, the alkene is selected from the group consisting of $PhC(CH_3)=CH_2$, $Ph_2C=CH_2$, (Z)-PhHC=CHPh, (E)-PhHC=CHPh, and $Ph_2C=CPh_2$.

In addition, the alkene may be a monounsaturated or polyunsaturated alkene. In some embodiment, the alkene is a mono or poly-unsaturated fatty acid or a fatty acid derivative, which is preferably derived from a natural source. Non-limiting examples of alkenes include monounsaturated fatty acids, polyunsaturated fatty acids, monounsaturated fatty alcohols, polyunsaturated fatty alcohols, monounsaturated amides, polyunsaturated amides, monounsaturated esters, polyunsaturated esters, monounsaturated nitriles and polyunsaturated nitriles, including all isomers thereof.

Non-limiting examples of alkenes include R-X wherein R is a mono or polyunsaturated alkenyl, and X=COOH, COOR', $CONH_2$, CONHR', CON(R')$_2$, CN, OH or $NH_2$ wherein R' is independently at each occurrence an alkyl, Examples include fatty acids (R—COOH) such as oleic acid, elaidic acid, linoleic acid (alpha or gamma), linolenic acid, eicosapentaenoic acid, docosahexaenoic acid, arachidonic acid, palmitic acid, palmitoleic acid, stearic acid, myristic acid, lauric acid, and tetradec-7-enoic acid; or an amine (X=$NH_2$), amide (X=$CONH_2$, CONHR' or CON(R')$_2$), alcohol (X=OH), ester (X=COOR') or nitrile (X=CN) derivative of any of the foregoing fatty acids. Each possibility represents a separate embodiment of the present invention. It is understood by a person of skill in the art that any other mono or polyunsaturated alkene can be used as a starting material in the process of the invention.

As used herein and in the appended claims the singular forms "a", "an," and "the" include plural references unless the content clearly dictates otherwise.

The principles of the present invention are demonstrated by means of the following non-limitative examples.

EXPERIMENTAL DETAILS SECTION

Example 1

Conversion of Alkenes to Aldehydes/Ketones with $Q_q\{\alpha_2\text{-TM(NO}_2)P_2W_{17}O_{61}\}$ A reaction of 0.156 M Q'$_8$$\{\alpha2$-Co(NO$_2$)P$_2$W$_{17}$O$_{61}\}$ with 0.078 M trans-stilbene in 0.5 mL of DCM/acetone (80/20, vol %) under Ar at 295 K yielded benzaldehyde as the sole product at 80% conversion by gas chromatographic (GC) analysis. In order to verify that Q'=[(C$_8$H$_{17}$)$_3$CH$_3$N—NO$_2$]$^+$ was not involved in this oxidative cleavage reaction and that the Co(III)-NO$_2$ moiety was responsible for the reaction observed, two control reactions were performed. The first was simply the reaction of trans-stilbene with Q'Cl, and the second involved the addition of 8 equiv of Q'Cl to the Co(II)-aqua species, Q$_8$$\{\alpha2$-Co$^{II}$(H$_2$O)P$_2$W$_{17}$O$_{61}\}$, and then its reaction with trans-stilbene. In neither case was any formation of benzaldehyde observed.

Figure 1:
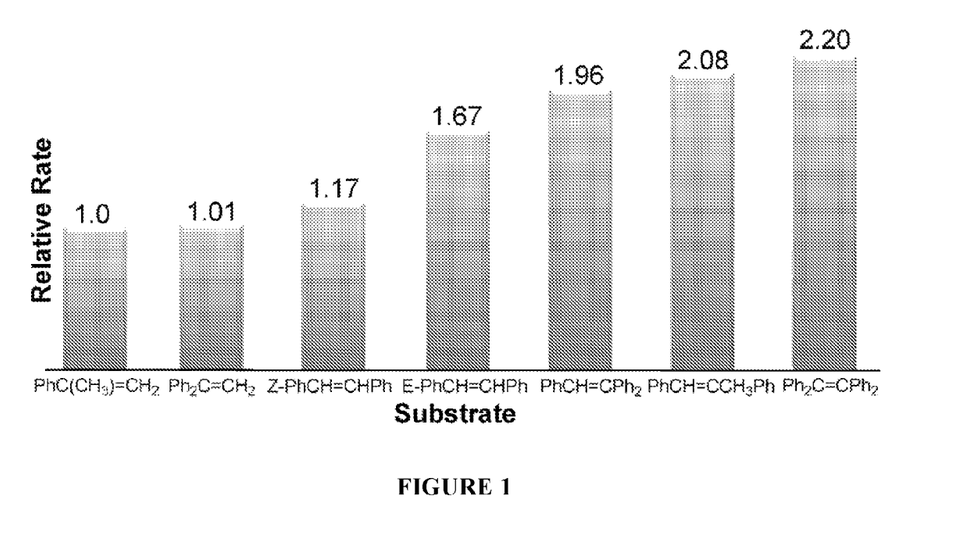
FIG. 1. Relative rate of oxidation of phenyl substituted alkene substrates by $Q_8\{\alpha_2\text{-Co}(NO_2)P_2W_{17}O_{61}\}$. Q=trioctylmethylammonium and/or the $NO_2$ adduct thereof. Reaction conditions: 62.5 mM substrate, 15.6 mM $Q_8\{\alpha_2\text{-Co}(NO_2)P_2W_{17}O_{61}\}$ in 80/20 vol/vol % DCM/acetone, Ar, 295 K.

It was demonstrated that various Wells-Dawson type polyoxometalates $\{\alpha_2$-TM(NO$_2$)P$_2$W$_{17}$O$_{61}\}^q$ where TM=Fe, Mn, Co, Ni, Cu, are reactive for the oxidative cleavage of alkenes in stoichiometric reactions under anaerobic conditions. For example, a series of alkenes was reacted with Q$_8$$\{\alpha_2$-Co(NO$_2$)P$_2$W$_{17}$O$_{61}\}$ (Q=trioctylmethylammonium and/or the NO$_2$ adduct thereof) to yield the aldehyde/ketone product only (FIG. 1).

The order of reactivity, as determined by the relative rate of reaction was 1,1-disubstituted alkenes<1,2-disubstituted alkenes<1,1,2-trisubstituted alkenes<tetraphenylethene. Trans-stilbene was more reactive than the cis-isomer. Oxidation of mono-substituted alkene such as styrene was slower and was less selective to benzaldehyde.

Figure 4:
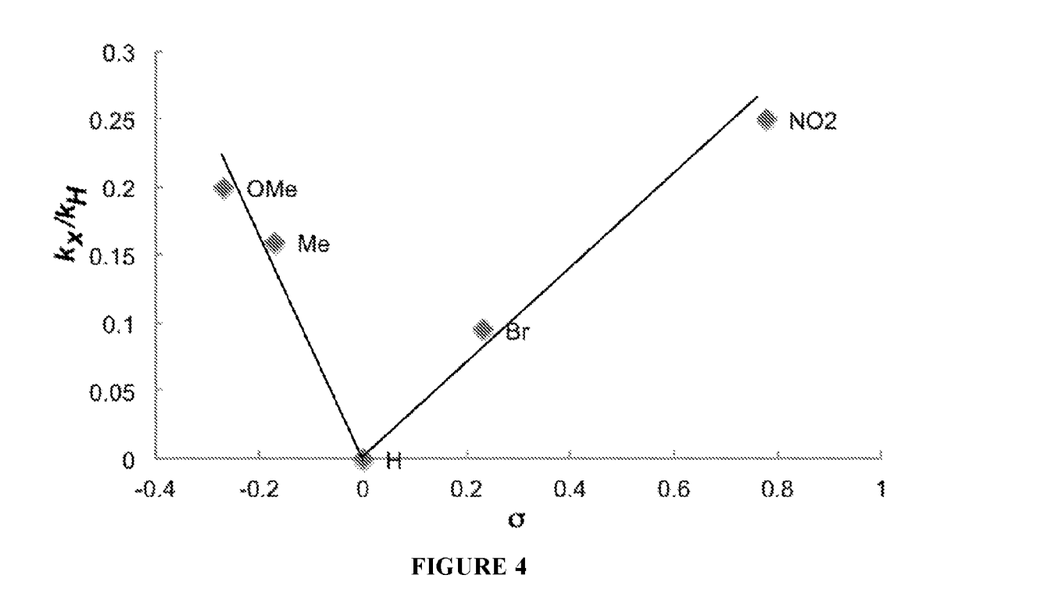
FIG. 4. Hammett plot for oxidative cleavage of trans-stilbene derivatives (62.5 mM) by $Q'_8\{\alpha_2\text{-Co}(NO_2)$ $P_2W_{17}O_{61}\}$ (15.6 mM). Reactions were carried out in DCM/acetone-$d_6$ (80/20, vol %) under Ar at 295 K.

Using various substituted trans-stilbene derivatives led to a Hammett plot that showed a change in the reaction mechanism from a positively charged transition state to a negatively charged one when going from electron-donating substituents (ρ=−0.77) to electron-withdrawing substituents (ρ=0.28) on the 4,4'-positions of the phenyl rings (FIG. 4). The low absolute ρ values indicate only a partial charge at the transition state and, therefore, more than likely a homolytic bond cleavage reaction rather than a more ionic heterolytic bond cleavage step.

The temperature dependence of the oxidative cleavage reaction was surveyed for trans-stilbene and its 4,4'-OMe and 4,4'-$NO_2$ derivatives as substrates (Table 1). As can be seen, the activation parameters, $\Delta G\ddagger$, $\Delta H\ddagger$, and $\Delta S\ddagger$, extracted from the Eyring plot, are very similar for all three substrates. Most significantly, the reaction is entropy controlled, the large negative value of $\Delta S\ddagger$ indicating a highly ordered transition state.

TABLE 1

Activation parameters for the reaction of trans-stilbene derivatives.

| Substituent | $\Delta G\ddagger_{298}$[b] | $\Delta H\ddagger_{298}$[b] | $\Delta S\ddagger_{298}$[c] |
|---|---|---|---|
| 4,4'-OMe | 20.5 | 2.4 | −60.5 |
| H | 20.7 | 3.1 | −59.1 |
| 4,4'-$NO_2$ | 20.4 | 2.3 | −60.8 |

[a]Reaction conditions:Trans-stilbene deivatives (62.5 mM) Q'$_8${α$_2$-Co(NO$_2$)P$_2$W$_{17}$O$_{61}$} (15.6 mM) in 0.5 mL DCM/acetone-d$_6$ 80/20 vol/vol % under Ar at 233-298 K;
[b]in kcal · mol$^{-1}$;
[c]in cal · mol$^{-1}$ · K$^{-1}$.

Figure 5:
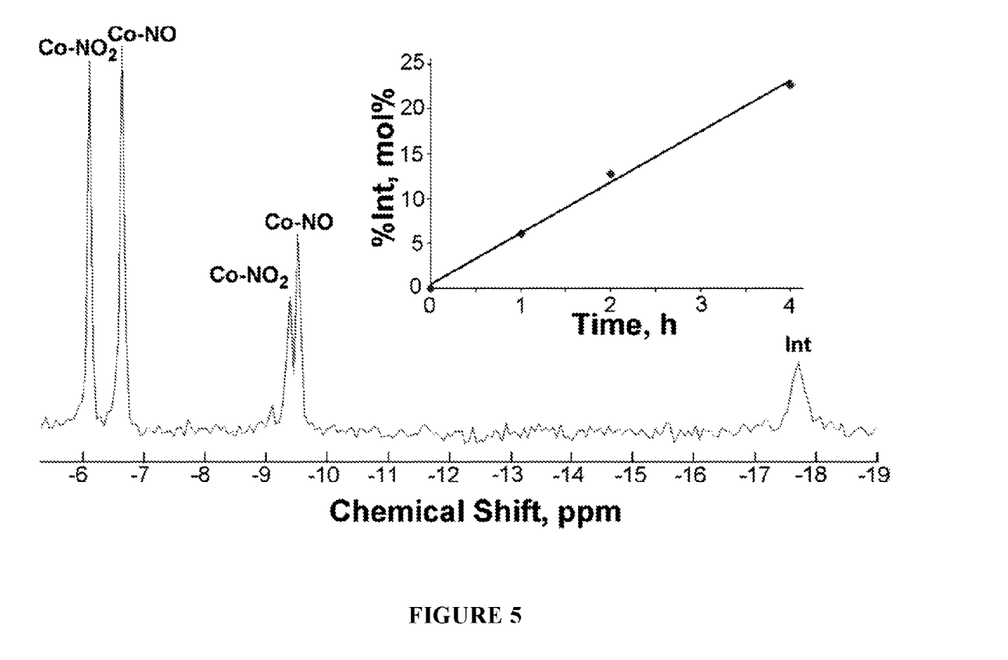
FIG. 5. $^{31}P$ NMR spectrum of a reaction mixture of $Q'^8\{\alpha 2\text{-Co}(NO_2)P_2W_{17}O_{61}\}^{8-}$ and trans-stilbene. Inset: the amount of intermediate species formed over time. The intermediate species is assigned to a $\{\alpha_2\text{-Co}(NO_2)P_2W_{17}O_{61}\}^{8-}$-trans-stilbene adduct that disappeared upon heating of the sample.
Figure 6:
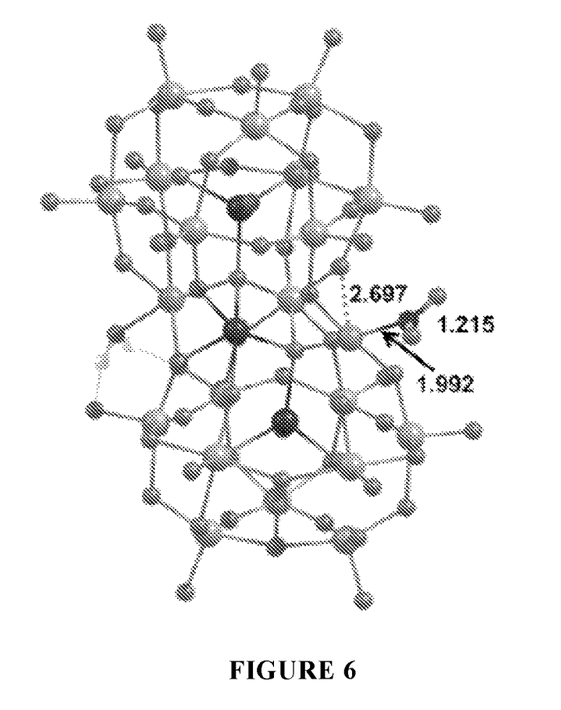
FIG. 6. Ball and stick structure representation for the model sandwich anion $[Cu(NO_2)Cu(H_2O)WZn_2(W_9O_{34})_2]^{12-}$. Selected distances are given in Å.

The fate of the {α$_2$-Co(NO$_2$)P$_2$W$_{17}$O$_{61}$}$^{8-}$ anion during the oxidative cleavage reaction of the trans-stilbene derivatives was followed by $^{31}$P NMR (FIG. 5). One may observe the formation of the nitrosyl product, {α$_2$-Co(NO)P$_2$W$_{17}$O$_{61}$}$_{8-}$, which has a spectrum, δ=−6.7 and 9.6 ppm, identical to that of a separately prepared compound. In addition, an intermediate species, Int, was observed that is assigned to a {α2-Co(NO$_2$)P$_2$W$_{17}$O$_{61}$}$^{8-}$-trans-stilbene adduct that disappeared upon heating of the sample. The amount of Int increases as the reaction continues (FIG. 5, inset). The peak width, the upfield chemical shift and position, and the absence of a complementary peak attributable to the phosphorus atom vicinal to the cobalt center argue for an intermediate in which it is reasonable that electron density is transferred from the double bond of the trans-stilbene to the polyoxometalate; that is, it is a Co(II) species. Further evidence for this assignment came from the integration of the combined {α2-Co(NO)—P$_2$W$_{17}$O$_{61}$}$^{8-}$ and Int peaks, which showed a conversion commensurate with the conversion observed by GC analysis. Next, a catalytic reaction using $O_2$ as the terminal oxidant was performed as described in Scheme 1. Surveying the reactivity of nitrosyl ligated compounds revealed that the copper substituted compound, Q$_8${α$_2$-Cu(NO)P$_2$W$_{17}$O$_{61}$} did slowly react with $O_2$ at slightly elevated temperatures of 65° C. to yield Q$_8$ {α$_2$-Cu(NO$_2$)P$_2$W$_{17}$O$_{61}$}. Measurement of the kinetics of the reaction of $O_2$ and Q$_8${α$_2$-Cu(NO)—P$_2$W$_{17}$O$_{61}$} to give Q$_8${α$_2$-Cu(NO$_2$)P$_2$W$_{17}$O$_{61}$} showed that the reaction was second order in Q$_8${α2-Cu(NO)P$_2$W$_{17}$O$_{61}$} and zero order in $O_2$.

It was observed that the aforementioned polyoxometalate was less stable at elevated temperatures, undergoing demetalation of the Cu center and formation of the lacunary species Q$_{10}${α$_2$-P$_2$W$_{17}$O$_{61}$}. Accordingly, the more stable sandwich type compounds, {[(TM(L)]$_2$WZn(ZnW$_9$O$_{34}$)$_2$}$^{12}$, were used for the catalytic reactions.

Example 2

Figure 2:
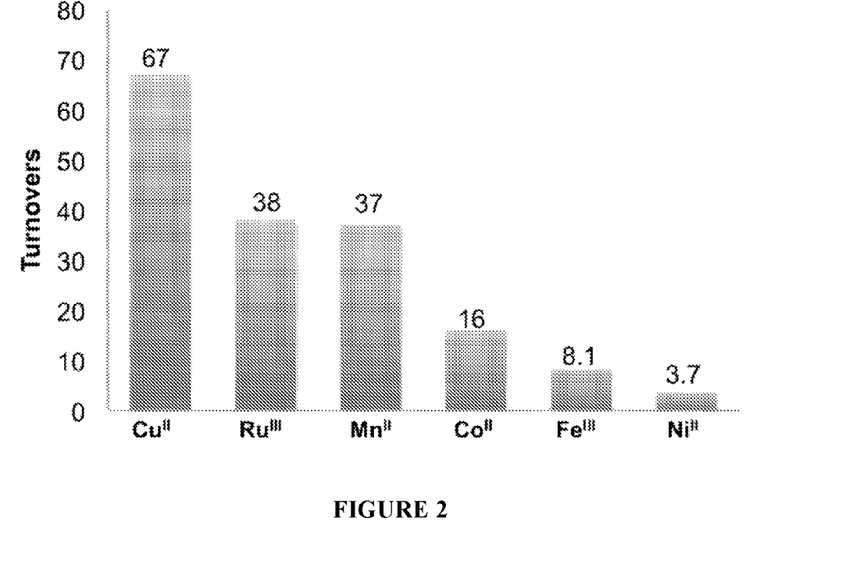
FIG. 2. Turnovers after 1 hr for the oxidation of 0.32 M trans-stilbene catalysed by 0.32 mM $Q_{12}\{ZnWTM_2(NO_2)_2(ZnW_9O_{34})_2\}$ in 9 mL MeCN, 2 bar $O_2$, 85° C. Q=trioctylmethylammonium and/or the $NO_2$ adduct thereof.

Conversion of Alkenes to Aldehydes/Ketones with Q$_q${[(TM(NO$_2$)]$_2$WZn(ZnW$_9$O$_{34}$)$_2$ Q$_q${[(TM(NO$_2$)]$_2$WZn(ZnW$_9$O$_{34}$)$_2$} complexes were prepared for TM=Cu, Mn, Ru, Fe, Co, and Ni and Q=trioctylmethylammonium and/or the $NO_2$ adduct thereof and reacted with trans-stilbene in the presence of $O_2$ (FIG. 2). The results show that the Cu substituted compound was the most reactive catalyst. This catalyst was thus used for the remaining studies.

Under $O_2$ pressure at 85° C., a control reaction in acetonitrile with the aqua complex, Q$_{12}${ZnWCu$_2$(H$_2$O)$_2$(ZnW$_9$O$_{34}$)$_2$}, Q=trioctylmethylammonium and/or the $NO_2$ adduct thereof showed no activity. However, the nitrosyl compounds Q$_{12}${ZnWCu$_2$(NO)$_2$(ZnW$_9$O$_{34}$)$_2$} did lead to efficient oxidation of trans-stilbene in the presence of $O_2$ (Scheme 2).

Scheme 2: Oxidative Cleavage of trans-stilbene Catalysed by Q$_{12}${ZnWCu$_2$(NO)$_2$(ZnW$_9$O$_{34}$)$_2$}.

Q = trioctylmethylammonium.

It was observed, however, that organic nitro compounds could be used as solvents/reagents in the oxidative cleavage reactions. In Scheme 3, a comparison was made between the reaction of aryl substituted ethenes catalysed by the nitro ligated compound, Q$_{12}${ZnWCu$_2$(NO$_2$)$_2$(ZnW$_9$O$_{34}$)$_2$}, Q=the $NO_2$ adduct of trioctylmethylammonium, carried out in acetonitrile (=System A) and a reaction catalysed by aqua compound Q$_{12}${ZnWCu$_2$(H$_2$O)$_2$(ZnW$_9$O$_{34}$)$_2$} Q=trioctylmethylammonium carried out in nitroethane (=System B). The reactions carried out in nitroethane gave significantly higher conversions and thus aldehyde products tended to be further oxidized to benzoic acid derivatives. It should be noted, however that increasing the pressure to 3 bar $O_2$ for reactions carried out using system B, raised the conversions to >90% with little change in reaction selectivity. Only in the case of cis- and trans-stilbene was nitration at the double bond observed. Trans-stilbene oxide could be further oxidized to benzaldehyde, but the diketone benzil was not reactive. Therefore, the former may be an intermediate in the reaction although in the stoichiometric reactions it was not observed.

Furthermore, it was observed that $O_2$ was required when nitroethane was used as a solvent. Use of acetonitrile/nitroethane as solvents with $Q_{12}\{ZnWCu_2(H_2O)_2(ZnW_9O_{34})_2\}$ Q=trioctylmethylammonium as catalyst was also efficient; the kinetic profiles showed that reactions were dependent on the nitroethane concentration.

Ar = 4MeOPh
System A (values left of slash)
0.065 mmol substrate, 5 mol% $Q_{12}\{ZnWCu_2(H_2O)_2(ZnW_9O_{34})_2\}$ Q = trioctylmethylammonium, 0.5 mL $EtNO_2$, 2 bar $O_2$, 85° C.
System B (values right of slash)
0.065 mmol substrate, 5 mol% $Q_{12}\{ZnWCu_2(NO_2)_2(ZnW_9O_{34})_2\}$ Q = trioctylmethylammonium and/or $NO_2$ adduct thereof, 0.5 mL MeCN, 2 bar $O_2$, 85° C.

The reaction with nitroethane as solvent or reagent was especially intriguing and raised the hypothesis that $Q_{12}\{ZnWCu_2(H_2O)_2(ZnW_9O_{34})_2\}$ in the presence of $O_2$ catalysed the formation of $NO_2$, which would then yield a $Cu-NO_2$ active species. Mechanistic studies indeed provide support for formation of $NO_2$ from nitroethane under the aerobic reaction conditions noted in Scheme 3 (data not shown).

A comparison of reaction with various nitroalkanes, $RNO_2$, as solvent where R=Me, Et, i-Pr, and t-Bu (5% $Q_{12}[ZnWCu^{II}_2(H_2O)_2(ZnW_9O_{34})_2]$ Q=trioctylmethylammonium, 0.065 mmol trans-stilbene $R-NO_2$ 0.5 mL, $O_2$ 3 bar, 85° C., 1 h) showed conversions 88% (Et)~85% (Me)>40% (i-Pr)>1% (t-Bu).

Example 3

Conversion of Methyloleate to Aldehydes/Ketones with $Q_{12}\{[(Cu(NO_2)]_2WZn(ZnW_9O_{34})_2$ It was shown noted above that $NO_2$ bound to a copper substituted sandwich type polyoxometalate efficiently catalysed the oxidative cleavage of arylated ethenes, when $NO_2$ was used a reagent or formed in situ either by oxidation of a nitrosyl substituted precursor or via decomposition of a nitroalkane under reaction conditions. The scope of the reaction for further substrate types was investigated. One interesting example is the oxidation of a bio-renewable based substrate, such as the methyloleate. Thus, the aerobic oxidative cleavage of methyloleate to yield the aldehyde, methyl-8-formyl-octanoate, could be a very accessible pathway to 9-amino methylnonanoate that could be used to make nylon 9. According to Scheme 4, greater than 90% yields of aldehyde products, nonanal and methyl-8-formyl-octanoate were attainable using nitroethane as solvent at 85° C., or using a minimal amount of $NO_2$ with propionic acid as solvent at 125° C. There was only slight formation, <3% of epoxide and carboxylic acids and no nitration products were observed.

Scheme 4. Oxidative Cleavage of Methyloleate.

Q = trioctylmethylammonium and/or $NO_2$ adduct thereof

Example 4

Polyoxometalate Synthesis $K_8\{\alpha_2\text{-}TM(H_2O)P_2W_{17}O_{61}\}$ where TM=$Co^{II}$, $Cu^{II}$ were prepared by the known literature method, as were the $Na_q\{ZnWTM_2(H_2O)_2(ZnW_9O_{34})_2\}$ compounds for TM=$Mn_{II}$ $Fe^{III}$, $Co^{II}$, $Ni^{II}$ and $Cu^{II}$.

Figure 3:
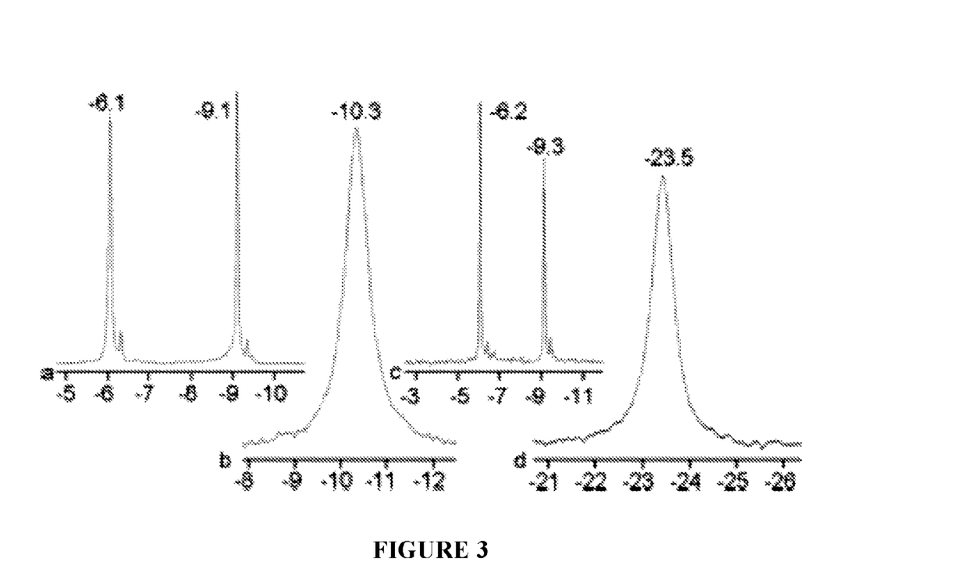
FIG. 3. $^{31}P$ NMR spectra of 48 mM $\{\alpha 2\text{-M}(L)P_2W_{17}O_{61}\}^{8-}$ in DCM/acetone-$d_6$ (80/20 vol %). (a) M=Cu; L=$NO_2$. (b) M=Cu; L=$H_2O$. (c) M=Co; L=$NO_2$. (d) M=Co; L=$H_2O$.

Aqua ligated polyoxometalates. $Q_8\{\alpha_2\text{-}TM(H_2O)P_2W_{17}O_{61}\}$ where Q=trioctylmethylammnonium were prepared by dissolving 200 mg of $K_8\{\alpha_2TM(H_2O)P_2W_{17}O_{61}\}$ in 20 mL $H_2O$ at room temperature. Eight equivalents of trioctylmethylammonium chloride (133 mg) dissolved in 20 mL dichloromethane were added and the biphasic mixture was vigorously stirred. The solvent was removed by evacuation from the lower organic phase to dryness, affording brown TM=Co$^{II}$ or green TM=Cu$^{II}$ oil with yields of 95-100%. $^{31}$P NMR (85% H$_3$PO$_4$ external standard): TM=Co$^{II}$ −23.5 ppm, TM=Cu$^{II}$ −10.3 ppm (FIG. 3). Visible spectra: $\lambda_{max}$, nm ($\epsilon$, cm$^{-1}$M$^{-1}$) for M=Co$^{II}$ 552 (96); M=Cu$^{II}$ 722 (48). Thermogravimetric measurements for both Q$_8${α$_2$-TM(H$_2$O)P$_2$W$_{17}$O$_{61}$} compounds showed a 42% mass loss corresponding at up to 300° C. corresponding to 8 equivalents of Q per polyoxometalate unit.

Nitro ligated polyoxometalates. Q$_8${α$_2$-TM(NO$_2$)P$_2$W$_{17}$O$_{61}$} where Q trioctylmethylammonium and/or NO$_2$ adduct thereof were prepared by dissolving 300 mg Q$_8${α$_2$-TM(H$_2$O)P$_2$W$_{17}$O$_{61}$} in 1 mL dichloromethane in a 50 mL flask, which was evacuated from air by 3 freeze-pump-thaw cycles. Then, at 77 K, NO$_2$(g) was introduced into the flask under vacuum for 1-2 sec producing initially a blue hue in the flask. After thawing to room temperature, an orange-brown gas lies above the colored solution. The flask was purged with Ar for 30 min after swirling it for a few seconds. A purple (TM=Co) or turquoise (TM=Cu) oil in quantitative yield was obtained and stored under Ar. $^{31}$P NMR (85% H$_3$PO$_4$ external standard): M=Co −6.2 and −9.3 ppm, M=Cu −6.1 and −9.1 ppm (FIG. 3). Visible spectra: $\lambda_{max}$, nm ($\epsilon$, cm$^{-1}$M$^{-1}$) for TM=Co 542 (81); M=Cu 783 (22).

Q$_q${[(TM(NO$_2$)]$_2$WZn(ZnW$_9$O$_{34}$)$_2$} compounds were prepared for TM=Cu, Mn, Ru, Fe, Co, and Ni in an identical fashion from Na$_q${ZnWTM$_2$(H$_2$O)$_2$(ZnW$_9$O$_{34}$)$_2$} starting materials. Thus, Q$_q${[(TM(NO$_2$)]$_2$WZn(ZnW$_9$O$_{34}$)$_2$} where Q=trioctylmethylammnonium were prepared by dissolving 200 mg of Na$_q${ZnWTM$_2$(H$_2$O)$_2$(ZnW$_9$O$_{34}$)$_2$} in 20 mL H$_2$O at room temperature. Twelve equivalents of trioctylmethylammonium chloride (200 mg) dissolved in 20 mL dichloromethane were added and the biphasic mixture was vigorously stirred. The solvent was removed by evacuation from the lower organic phase to dryness, affording Q$_q${ZnWTM$_2$(H$_2$O)$_2$(ZnW$_9$O$_{34}$)$_2$}. Q$_q${ZnWTM$_2$(H$_2$O)$_2$(ZnW$_9$O$_{34}$)$_2$} was then reacted with NO$_2$(g) at 77 K by its introduction into the flask under vacuum for 1-2 sec producing initially a blue hue in the flask. After thawing to room temperature, an orange-brown gas lies above the colored solution. The flask was purged with Ar for 30 min after swirling it for a few seconds. Q$_q${[TM(NO$_2$)]$_2$WZn(ZnW$_9$O$_{34}$)$_2$} were obtained in greater than 90% yield and stored under Ar.

Nitrosyl ligated polyoxometalates. Q$_8${α$_2$-TM(NO)P$_2$W$_{17}$O$_{61}$} where Q=trioctylmethylammonium were prepared by dissolving 80 mg Q$_8${α$_2$-TM(H$_2$O)P$_2$W$_{17}$O$_{61}$} in 1 mL dichloromethane in a 50 mL flask, which was evacuated from air by 3 freeze-pump-thaw cycles. In parallel, NO(g) was prepared by adding 900 mg NaNO$_2$ (97%) to 5 mL glacial acetic acid. If some NO$_2$ was formed (brown color) it was removed by a gentle flow of Ar. By syringe 20 mL of the NO gas was injected to the polyoxometalate solution and shaken manually for 5 min with an accompanying color change. The flask was purged with Ar for 30 min. After removal of the solvent After pale-blue (TM=Co) or yellow (TM=Cu) oils were obtained in quantitative yield and stored under Ar. $^{31}$P NMR (85% H$_3$PO$_4$ external standard): TM=Co −6.7 and −9.6 ppm, TM=Cu −6.6 and −9.9 ppm. Visible spectra: $\lambda_{max}$, nm ($\epsilon$, cm$^{-1}$M$^{-1}$) for TM=Co 685 (108); TM=Cu 400 shoulder.

Oxidation Reactions.

Catalytic oxidation reactions were carried out in 25 mL ace glass pressure tubes. The tubes were charged with the catalyst, substrate and solvent in the specified amounts; air was purged and then pressurized with O$_2$ and heated in a temperature controlled oil bath. At each relevant time period, an aliquot was taken, dissolved in 0.2 mL DCM and then analysed by GC/GC-MS.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A process for the preparation of aldehydes and/or ketones from alkenes, comprising the step of contacting said alkene with a nitro coordinated polyoxometalate catalyst comprising a transition metal (TM), or a solvate thereof, thereby generating the aldehydes and/or ketones.

2. The process according to claim 1, wherein said nitro coordinated polyoxometalate catalyst forms a transition metal-NO$_2$, complex which catalyses C=C bond cleavage of the alkene, thereby generating the aldehydes and/or ketones.

3. The process according to claim 1, wherein said nitro coordinated polyoxometalate is formed either in situ with said alkene or independent from said alkene; wherein said nitro coordinated polyoxometalate is formed by reacting a polyoxometalate precatalyst comprising transition metal (TM), or a solvate thereof with nitrogen dioxide (NO$_2$).

4. The process of claim 3, wherein said NO$_2$ is added as a gas or in the form of its dimer N$_2$O$_4$, and wherein the reaction is conducted under aerobic or anaerobic conditions.

5. The process according to claim 1, wherein said nitro coordinated polyoxometalate is formed in situ with said alkene or independent from said alkene; wherein said nitro coordinated polyoxometalate is formed by reacting polyoxometalate precatalyst and a nitroalkane under aerobic conditions.

6. The process according to claim 5, wherein said process in situ comprises contacting said alkene with an aqua (H$_2$O) or other ligand coordinated polyoxometalate precatalyst in the presence of a nitroalkane and molecular oxygen (O$_2$), wherein the nitroalkane decomposes to generate NO$_2$ in situ and thereby said nitro coordinated polyoxometalate catalyst is formed.

7. The process according to claim 5, wherein the nitroalkane is represented by the structure RNO$_2$ wherein R is a C$_1$-C$_3$alkyl.

8. The process according to claim 1, wherein said nitro polyoxometalate is formed in situ with said alkene or independent from said alkene; wherein said nitro coordinated polyoxometalate is formed by reacting a nitrosyl (NO) coordinated polyoxometalate precatalyst under aerobic conditions or oxygen (O$_2$) to yield nitro coordinated polyoxometalate.

9. The process according to claim 1, wherein said process produces a nitrosyl (NO) coordinated polyoxometalate which is regenerated under aerobic conditions to produce a nitro (NO$_2$) coordinated polyoxometalate.

10. The process according to claim 1, wherein said alkene is non-cyclic alkene.

11. The process according to claim 1, wherein said alkene is from a synthetic or natural, bio-renewable origin.

12. The process according to claim 1, wherein the alkene is a 1-monosubstituted alkene, 1,1-disubstituted alkene, a 1,2-disubstituted alkene, a 1,1,2-trisubstituted alkene or a 1,1,2,2-tetrasubstituted alkene.

13. The process according to claim 12, wherein the alkene is represented by formula R$^1$R$^2$C=CR$^3$R$^4$ wherein R$^1$-R$^4$ is each independently H, optionally substituted C$_1$-C$_{20}$ alkyl, optionally substituted aryl, optionally substituted cycloalkyl, optionally substituted heterocycloalkyl, or optionally substituted heteroaryl, wherein at least one of $R^1$-$R^4$ is other than H.

14. The process according to claim 12, wherein said alkene is selected from the group consisting of PhC(CH$_3$)=CH$_2$; Ph$_2$C=CH$_2$; (Z)-PhCH=CHPh, (E)-PhCH=CHPh, and Ph$_2$C=CPh$_2$.

15. The process according to claim 12, wherein said alkene is selected from the group consisting of monounsaturated fatty acids, polyunsaturated fatty acids, monounsaturated fatty alcohols, polyunsaturated fatty alcohols, monounsaturated amides, polyunsaturated amides, monounsaturated esters, polyunsaturated esters, monounsaturated nitriles and polyunsaturated nitriles, including all isomers thereof.

16. The process according to claim 1, wherein said polyoxometalate catalyst is a polyoxoanion salt polyoxometalate represented by the structure of formula I:

Q$_q$[X$_x$M$_m$TM$_n$L$_l$O$_y$F$_z$]

or a solvate thereof, wherein
X is a metal or non-metal heteroatom, a proton or combination thereof;
M is an addenda atom selected from the group consisting of tungsten (W), molybdenum (Mo), niobium (Nb), and vanadium (V), and any combination thereof;
TM is a transition metal selected from the group consisting of chromium (Cr), iron (Fe), manganese (Mn), cobalt (Co), nickel, (Ni), copper (Cu), zinc (Zn), ruthenium (Ru), palladium (Pd), platinum (Pt), iridium (Ir), rhodium (Rh) and any combination thereof;
L is nitrogen dioxide (NO$_2$);
Q is a counter-cation selected from the group consisting of an alkali metal cation, an alkaline earth metal cation, a transition metal cation, an organic cation, a substituted or unsubstituted quaternary ammonium cation, an adduct of said quaternary ammonium cation with NO$_2$, a substituted or unsubstituted quaternary phosphonium cation, an adduct of said quaternary phosphonium cation with NO$_2$, and any combination thereof;
O is oxygen;
F is fluorine;
x is an integer between 0 and 6;
m is an integer between 4 and 200;
n is an integer between 1 and 10;
l is an integer between 1 and 10;
y is an integer between 5 and 1000;
q is an integer between 0 and 30; and
z is an integer between 0 to 20.

17. The process according to claim 3, wherein said polyoxometalate precatalyst is a polyoxoanion salt polyoxometalate represented by the structure of formula I:

Q$_q$[X$_x$M$_m$TM$_n$L$_l$O$_y$F$_z$]

or a solvate thereof, wherein
X is a metal or non-metal heteroatom, a proton or a combination thereof;
M is an addenda atom selected from the group consisting of tungsten (W), molybdenum (Mo), niobium (Nb), and vanadium (V), and any combination thereof;
TM is a transition metal selected from the group consisting of chromium (Cr), iron (Fe), manganese (Mn), cobalt (Co), nickel, (Ni), copper (Cu), zinc (Zn), ruthenium (Ru), palladium (Pd), platinum (Pt), iridium (IT), rhodium (Rh) and any combination thereof;

L is absent or is a ligand selected from the group consisting of (ILO), hydroxyl (OH), a halide selected from F, Cl, Br and I; a pseudohalide selected from CN, OCN and SCN;
nitrosyl (NO), and any combination thereof;
Q is a counter-cation selected from the group consisting of an alkali metal cation, an alkaline earth metal cation, a transition metal cation, an organic cation, a substituted or unsubstituted quaternary ammonium cation, a substituted or unsubstituted quaternary phosphonium cation, and any combination thereof;
O is oxygen;
F is fluorine;
x is an integer between 0 and 6;
m is an integer between 4 and 200;
n is an integer between 1 and 10;
l is an integer between 0 and 10;
y is an integer between 5 and 1000;
q is an integer between 0 and 30; and
z is an integer between 0 to 20.

18. The process according to claim 16, wherein the polyoxometalate catalyst is a Wells-Dawson type polyoxometalate represented by the structure Q$_q$\{$\alpha_2$-TM(L)P$_2$W$_{17}$O$_{61}$\} or Q$_q$\{$\alpha_1$-TM(L)P$_2$W$_{17}$O$_{61}$\} or said polyoxometalate catalyst is Q$_q$\{[TM(L)]$_2$WZn(ZnW$_9$O$_{34}$)$_2$\} or Q$_q$\{[(TM(L)]$_2$WCo(CoW$_9$O$_{34}$)$_2$\} or said polyoxometalate is a Keggin type polyoxometalate represented by the structure Q$_q$\{XTM(L)M$_{11}$O$_{39}$\} or said polyoxometalate is a quasi Wells-Dawson polyfluoroxometalate represented by the structure Q$_q$\{X'H$_2$TM(L)W$_{17}$F$_6$O$_{55}$\}
wherein X, TM, L, Q, M and q are as defined in claim 16; and X' is Na.

19. The process according to claim 17, wherein said polyoxometalate precatalyst is a Wells-Dawson type polyoxometalate represented by the structure Q$_q$\{$\alpha_2$-TM(L)P$_2$W$_{17}$O$_{61}$\} or Q$_q$\{$\alpha_1$-TM(L)P$_2$W$_{17}$O$_{61}$\} or said polyoxometalate is Q$_q$\{[(TM(L)]$_2$WZn(ZnW$_9$O$_{34}$)$_2$\} or Q$_q$\{[(TM(L)]$_2$WCo(CoW$_9$O$_{34}$)$_2$\}; or said polyoxometalate is a Keggin type polyoxometalate represented by the following structure Q$_q$\{XTM(L)M$_{11}$O$_{39}$\} or said polyoxometalate is a quasi Wells-Dawson polyfluoroxometalate represented by the structure Q$_q$ \{X'H$_2$TM(L)W$_{17}$F$_6$O$_{55}$\} ; wherein X, TM, L, Q, M and q are as defined in claim 17 and X' is Na.

20. The process according to claim 16, wherein said TM is a transition metal selected from Cr, Mn, Fe, Co, Ni, Cu, Zn and Ru;
L is NO$_2$;
Q is a counter-cation selected from the group consisting of an alkali metal cation, an alkaline earth metal cation, a transition metal cation, an organic cation, a substituted or unsubstituted quaternary ammonium cation, an adduct of said quaternary ammonium cation with NO$_2$, a substituted or unsubstituted quaternary phosphonium cation, an adduct of said quaternary phosphonium cation with NO$_2$, and any combination thereof; and
q is an integer between 6 and 12.

21. The process according to claim 17, wherein said TM is a transition metal selected from Cr, Mn, Fe, Co, Ni, Cu, Zn and Ru;
L is $_2$O or NO;
Q is a counter-cation selected from the group consisting of an alkali metal cation, an alkaline earth metal cation, a transition metal cation, an organic cation, a substituted or unsubstituted quaternary ammonium cation, a substituted or unsubstituted quaternary phosphonium cation, and any combination thereof; and
q is an integer between 6 and 12.

22. The process according to claim 18, wherein the polyoxometalate catalyst is selected from the group consisting of $Q_8\{\alpha_2\text{-Cu}(NO_2)P_2W_{17}O_{61}\}$, $Q_8\{\alpha_1\text{-Cu}(NO_2)P_2W_{17}O_{61}\}$, $Q_{12}\{ZnWCu_2(NO_2)_2(ZnW_9O_{34})_2\}$, $Q_{12}\{CoWCu_2(NO_2)_2(CoW_9O_{34})_2\}$, $Q_9\{NaH_2Cu(NO_2)W_{17}F_6O_{55}\}$ and $Q_9\{NaH_2Mn(NO_2)W_{17}F_6O_{55}\}$.

23. The process according to claim 19, wherein the polyoxometalate precatalyst is selected from the group consisting of $Q_8\{\alpha_2\text{-Cu}(H_2O)P_2W_{17}O_{61}\}$, $Q_8\{\alpha_2\text{-Cu}(NO)P_2W_{17}O_{61}\}$, $Q_8\{\alpha_1\text{-Cu}(H_2O)P_2W_{17}O_{61}\}$, $Q_8\{\alpha_1\text{-Cu}(NO)P_2W_{17}O_{61}\}$, $Q_{12}\{ZnWCu_2(H_2O)_2(ZnW_9O_{34})_2\}$, $Q_{12}\{ZnWCu_2(NO)_2(ZnW_9O_{34})_2\}$, $Q_{12}\{CoWCu_2(H_2O)_2(CoW_9O_{34})_2\}$, $Q_{12}\{CoWCu_2(NO)_2(CoW_9O_{34})_2\}$, $Q_9\{NaH_2Cu(H_2O)W_{17}F_6O_{55}\}$, $Q_9\{NaH_2Mn(H_2O)W_{17}F_6O_{55}\}$, $Q_9\{NaH_2Cu(NO)W_{17}F_6O_{55}\}$ and $Q_9\{NaH_2Mn(NO)W_{17}F_6O_{55}\}$.

24. The process according to claim 18, wherein X is Na, proton, P, Si or As; M is Mo, W or any combination thereof, and q is 3-10.

25. The process according to claim 19, wherein X is Na, proton, P, Si or As; M is Mo, W or any combination thereof, and q is 3-10.

26. The process according to claim 16, wherein Q is trioctylmethylammonium or an $NO_2$ adduct thereof.

27. The process according to claim 16, wherein X is selected from the group consisting of Na, B, Al, Ga, In, Si, Ge, Sn, P, As, Sb, S, Se, Te, and a proton or any combination thereof.

28. The process according to claim 1, wherein the reaction is conducted in a solvent selected from the group consisting of aromatic hydrocarbons, nitriles, carboxylic acids, ketones, alcohols, halogenated hydrocarbons, nitroalkanes, ethers, dimethyl sulfoxide, amides, carboxylic acids, and esters.

29. The process according to claim 1, wherein the solvate is selected from the group consisting of a hydrate, a diethylether solvate, an acetonitrile solvate, a dimethylsulfoxide solvate, a tetrahydrofuran solvate, a methanol solvate and ethanol solvate.

30. A nitro coordinated polyoxometalate catalyst represented by the structure of formula I:

or a solvate thereof, wherein said nitro coordinated polyoxometalate catalyst forms a transition metal-$NO_2$ complex;
wherein
X is a metal or non-metal heteroatom, proton or any combination thereof;
M is an addenda atom selected from the group consisting of tungsten (W), molybdenum (Mo), niobium (Nb), and vanadium (V), and any combination thereof;
TM is a transition metal selected from the group consisting of chromium (Cr), iron (Fe), manganese (Mn), cobalt (Co), nickel, (Ni), copper (Cu), zinc (Zn), ruthenium (Ru), palladium (Pd), platinum (Pt), iridium (Ir), rhodium (Rh) and any combination thereof;
L is nitrogen dioxide ($NO_2$);
Q is a counter-cation selected from the group consisting of an alkali metal cation, an alkaline earth metal cation, a transition metal cation, an organic cation, a substituted or unsubstituted quaternary ammonium cation, an adduct of said quaternary ammonium cation with $NO_2$, a substituted or unsubstituted quaternary phosphonium cation, an adduct of said quaternary phosphonium cation with $NO_2$, and any combination thereof;
O is oxygen;
F is fluorine;
x is an integer between 0 and 6;
m is an integer between 4 and 200;
n is an integer between 1 and 10;
l is an integer between 1 and 10;
y is an integer between 5 and 1000;
q is an integer between 0 and 30; and
z is an integer between 0 to 20.

31. The catalyst of claim 30, wherein said catalyst of Formula I is represented by the following structures: $Q_q\{\alpha_2\text{-TM}(L)P_2W_{17}O_{61}\}$, $Q_q\{\alpha_1\text{-TM}(L)P_2W_{17}O_{61}\}$, $Q_q\{[(TM(L)]_2WZn(ZnW_9O_{34})_2\}$, $Q_q\{[(TM(L)]_2WCo(CoW_9O_{34})_2\}$, $Q_q\{XH_2TM(L)W_{17}F_6O_{55}\}$; or $Q_q\{XTM(L)M_{11}O_{39}\}$.

32. The catalyst of claim 31, wherein said catalyst is $Q_8\{\alpha_2\text{-Cu}(NO_2)P_2W_{17}O_{61}\}$, $Q_8\{\alpha_1\text{-Cu}(NO_2)P_2W_{17}O_{61}\}$, $Q_{12}\{ZnWCu_2(NO_2)_2(ZnW_9O_{34})_2\}$, $Q_{12}\{CoWCu_2(NO_2)_2(CoW_9O_{34})_2\}$, $Q_9\{NaH_2Cu(NO_2)W_{17}F_6O_{55}\}$ or $Q_9\{NaH_2Mn(NO_2)W_{17}F_6O_{55}\}$.

* * * * *